US008680126B2

(12) United States Patent
Gil Santano et al.

(10) Patent No.: US 8,680,126 B2
(45) Date of Patent: Mar. 25, 2014

(54) FLUORINATED THIAZOLES FOR USE IN TREATING CANCER

(75) Inventors: Joan Gil Santano, Castelldefels (ES); Rodolfo Lavilla Grifols, Castelldefels (ES); Fernando Albericio Palomera, Barcelona (ES); Alba Pérez Perarnau, Sabadell (ES); Sara Preciado Gallego, L'Hospitalet de Llobregat (ES); Diana M$^a$ González Gironès, Bigues i Riells (ES); Daniel Iglesias Serret, Barcelona (ES); Rosario Ramón Albalate, L'Hospitalet de Llobregat (ES)

(73) Assignees: Universitat de Barcelona, Barcelona (ES); Fundacio Privada Institut d'Inbestigacio Biomedica de Bell Vitge, l'Hospitalet de Llobregat (ES); Fundacio Privada Institute de Recerca Biomedica de Barcelona, Barcelona (ES); Fundacio Privada Parc Cientific de Barcelona, Barcelona (ES)

( * ) Notice: Subject to any disclaimer, the term of this patent is extended or adjusted under 35 U.S.C. 154(b) by 0 days.

(21) Appl. No.: 13/820,480

(22) PCT Filed: Aug. 29, 2011

(86) PCT No.: PCT/ES2011/070605
§ 371 (c)(1),
(2), (4) Date: Mar. 1, 2013

(87) PCT Pub. No.: WO2012/028757
PCT Pub. Date: Mar. 8, 2012

(65) Prior Publication Data
US 2013/0190367 A1    Jul. 25, 2013

(30) Foreign Application Priority Data

Sep. 2, 2010   (ES) .................................. 201031314

(51) Int. Cl.
*A61K 31/425*  (2006.01)
*C07D 417/00*  (2006.01)

(52) U.S. Cl.
USPC .......................................... 514/365; 544/133

(58) Field of Classification Search
USPC .......................................... 514/365; 544/133
See application file for complete search history.

(56) References Cited

U.S. PATENT DOCUMENTS 8,217,037 B2 *   7/2012   Giordano et al. .......... 514/234.5
2009/0076101 A1 *  3/2009   Ferrigno et al. ............. 514/365
2009/0306073 A1 * 12/2009   Giordano et al. .......... 514/235.2

FOREIGN PATENT DOCUMENTS

WO   WO2004016622   2/2004

OTHER PUBLICATIONS

J.A. Seijas et al., Straightforward Microwave-assisted Synthesis of 2-thiazolines Using Lawesson's Reagent Under Solvent-free Conditions, 2008 (the year of publication is sufficiently earlier than the effective U.S. filing date and any foreign priority date so that the particular month of publication is not in issue), pp. 9280-9285, vol. 64, No. 39, Tetrahedron, Elsevier Science, Amsterdam, NL.
Couture et al., A Convenient and Concise Synthesis of 2,4-diaryl 2-thiazolines, 1995 (the year of publication is sufficiently earlier than the effective U.S. filing date and any foreign priority date so that the particular month of publication is not an issue), pp.809-811, vol. 8, Synlett, Thieme Medical Publishers, Inc., Stuttgart, DE.
H.Kurata et al., The First Synthesis of 2,2',5'2"-terthiazole, 2008 (the year of publication is sufficiently earlier than the effective U.S. filing date and any foreign priority date so that the particular month of publication is not an issue), pp. 2882-2884, Synlett, Georg Thieme Verlag KG, Stuttgart, Germany.
V.N.Kerr et al., Liquid Scintillators VII. 2,5-diaryl substituted thiazoles as liquid Scintillator solutes, 1959 (the year ot publication is sufficiently earlier than the effective U.S. filing date and any foreign priority date so that the particular month of publication is not in issue), pp. 1861-1864, vol. 24, Journal of Organic Chemistry, American Chemical Society, New York, US.
K. Dolling et al., Kristallin-flüssige Thiazole, 1979 (the year of publication is sufficiently earlier than the effective U.S. filing date and any foreign priority date so that the particular month of publication is not an issue), pp. 643-654, vol. 321, No. 4, Journal für praktische Chemie, Wiley-VCH, Heidelberg-Leipzig, Germany. (First paragraph English abstract).

(Continued)

*Primary Examiner* — Raymond Henley, III
(74) *Attorney, Agent, or Firm* — Peter B. Scull; Hamilton DeSanctis & Cha, LLP

(57) ABSTRACT

Compounds of formula (I) or their pharmaceutically acceptable salts, or their stereoisomers or mixtures of stereoisomers, where: $R_1$ is selected from the group consisting of: phenyl, and phenyl mono-, di-, or tri-substituted by a radical independently selected from the group consisting of F, Cl, Br, I, $(C_1-C_6)$-alkyl, COO—$(C_1-C_6)$-alkyl, and $(C_1-C_6)$-alkoxy; and $R_2$ is a radical selected from the same group as $R_1$, further including a phenyl substituted in 4-position by a radical independently selected from the group consisting of —O($CH_2$) CONH($CH_2)_3CH_3$ and O$CH_2$COOC($CH_3)_3$, a biphenyl-4-yl, thiazol-2-yl, and a thiazol-2-yl mono- or di-substituted by a radical selected from F and phenyl; inhibit cell proliferation of tumor cells independently of p53 protein and may also induce apoptosis in several tumor cells independently of p53 protein, being useful for the treatment of several types of cancer.

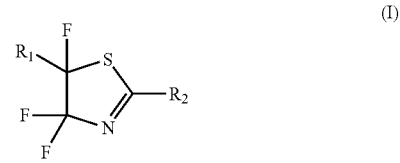

(I)

15 Claims, 7 Drawing Sheets

(56) References Cited

OTHER PUBLICATIONS

International Search Report and Written Opinion of the International Searching Authority, Search Report, Application No. PCT/ES2011/070605 issued by the Oficina Espanola De Patentes Y Marcas, Madrid, Spain, dated Jan. 27, 2012.

Translation of International Search Report and Written Opinion of the International Searching Authority, Search Report, Application No. PCT/ES2011/070605 issued by the Oficina Espanola De Patentes Y Marcas, Madrid, Spain, dated Jan. 27, 2012.

International Preliminary Report on Patentability, Application No. PCT/ES2011/070605 issued by The International Bureau of WIPO, Geneva, Switzerland, with translation (translation is of Written Opinion), dated Mar. 5, 2013.

* cited by examiner

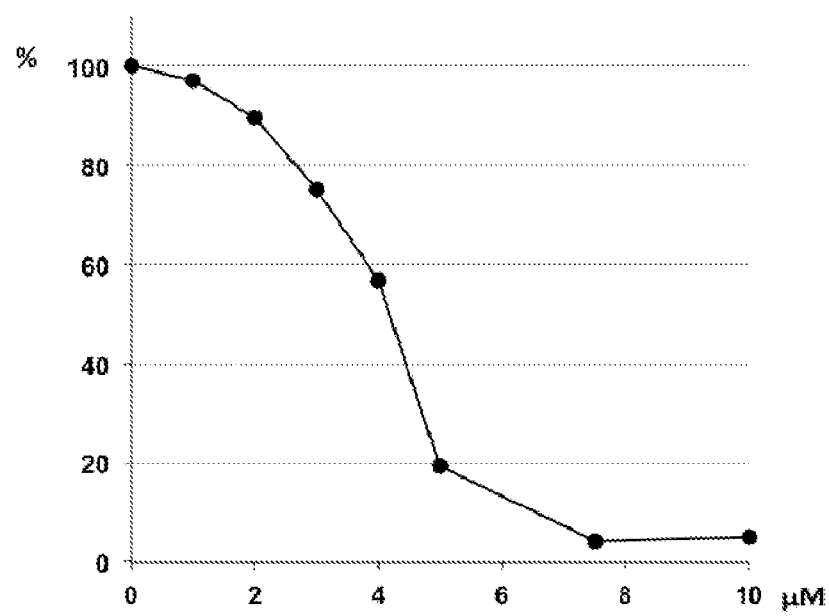
FIG. 1: Jurkat
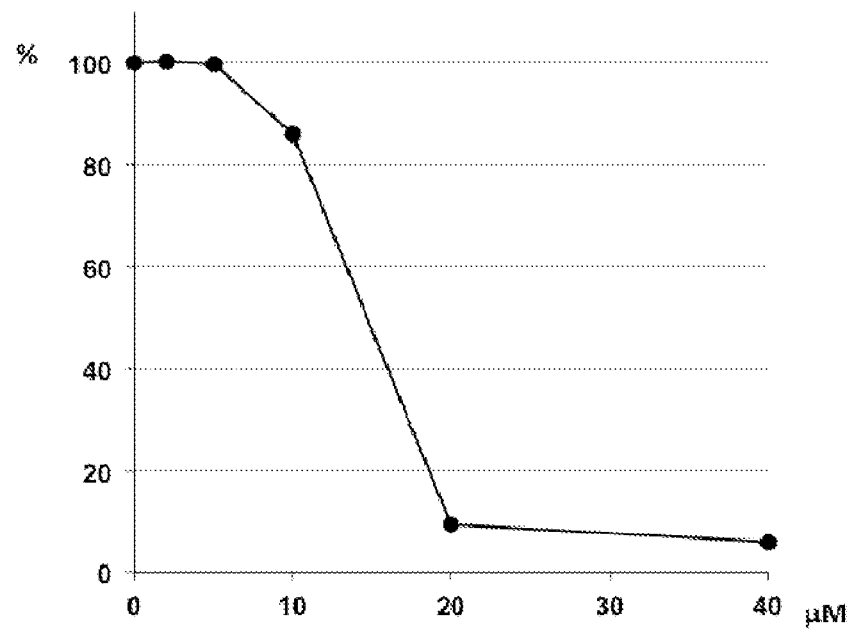
FIG. 2: HeLa

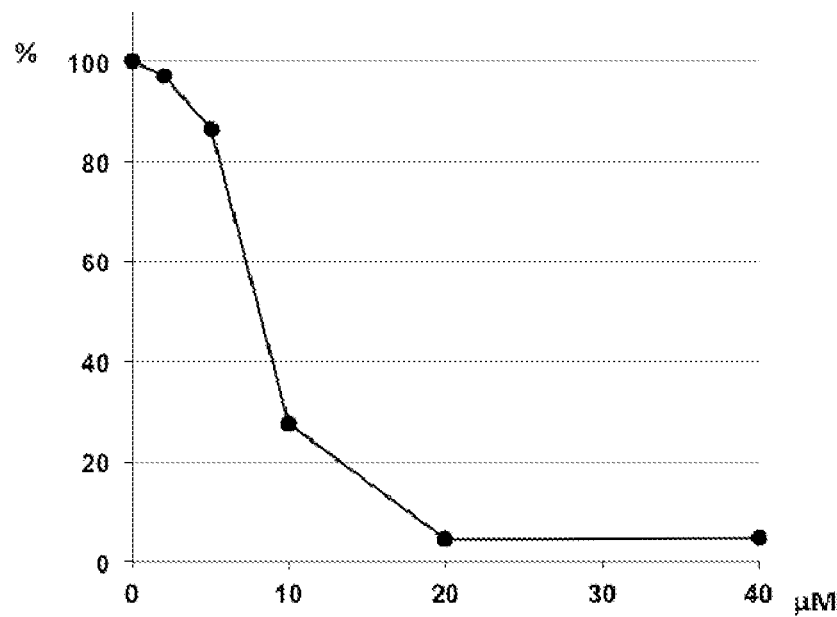
FIG. 3: TK6
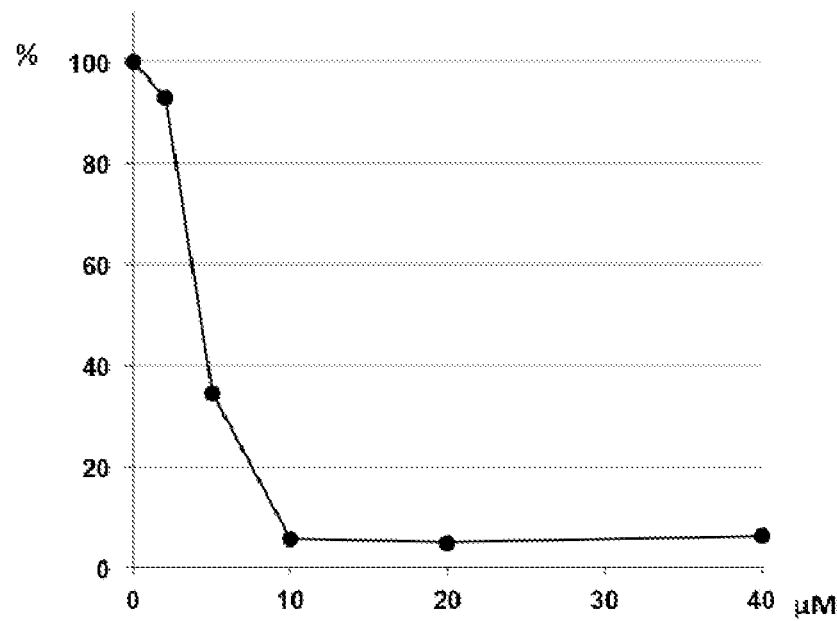
FIG. 4: Ramos

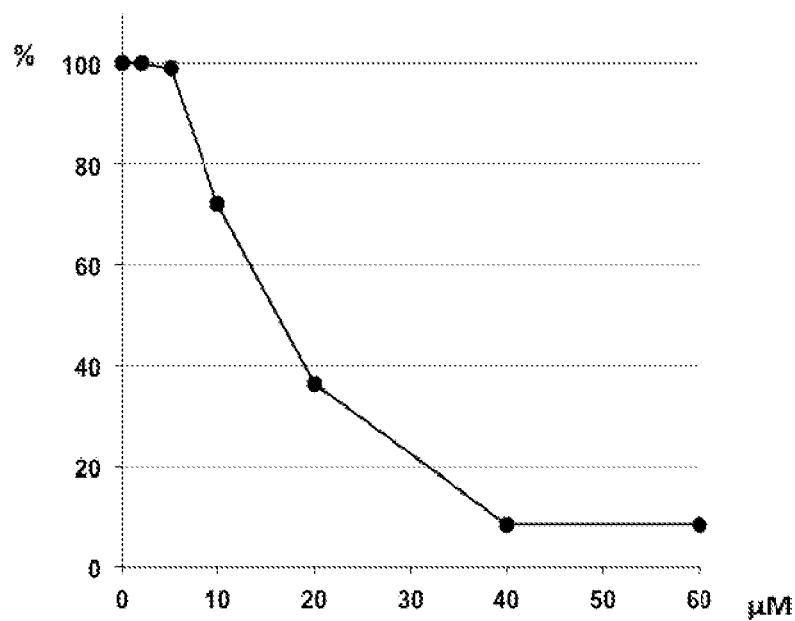
FIG. 5: MDA-MB-231
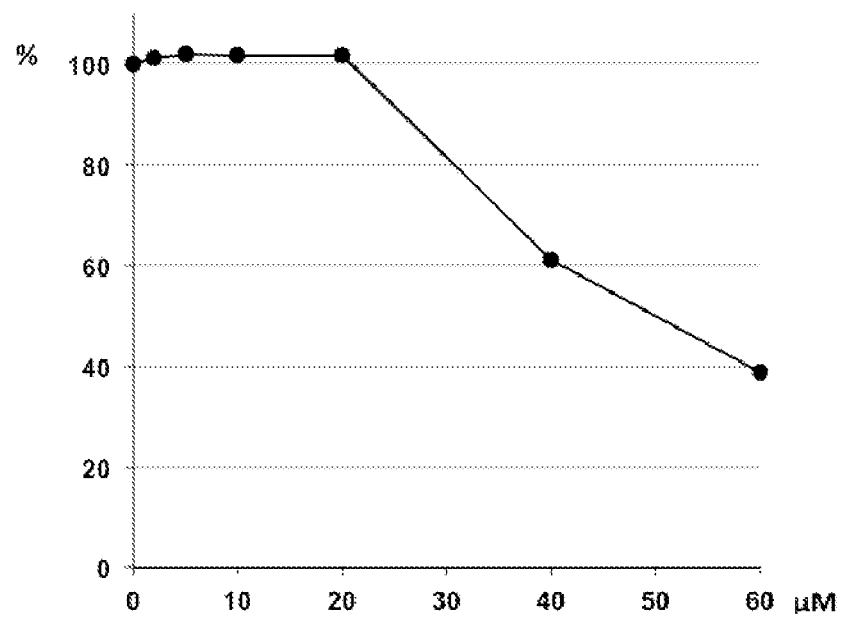
FIG. 6: T98-G

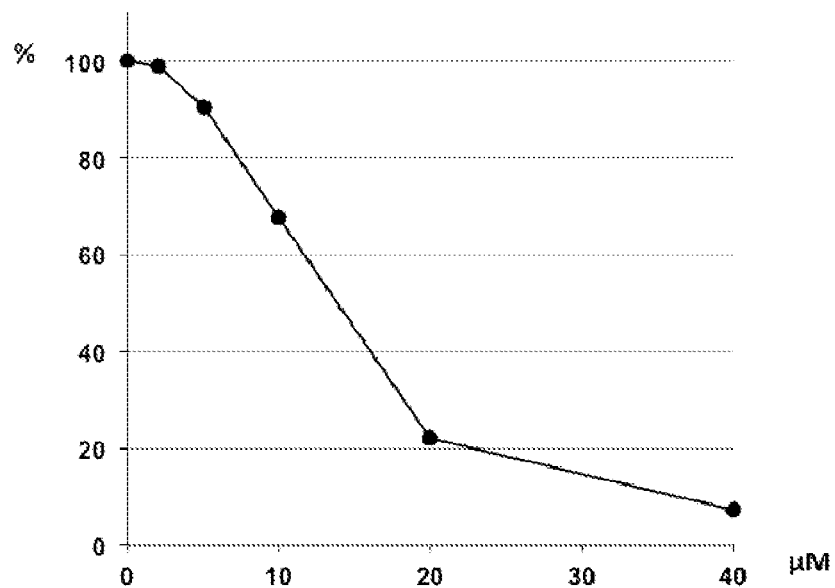
FIG. 7: Hep3B
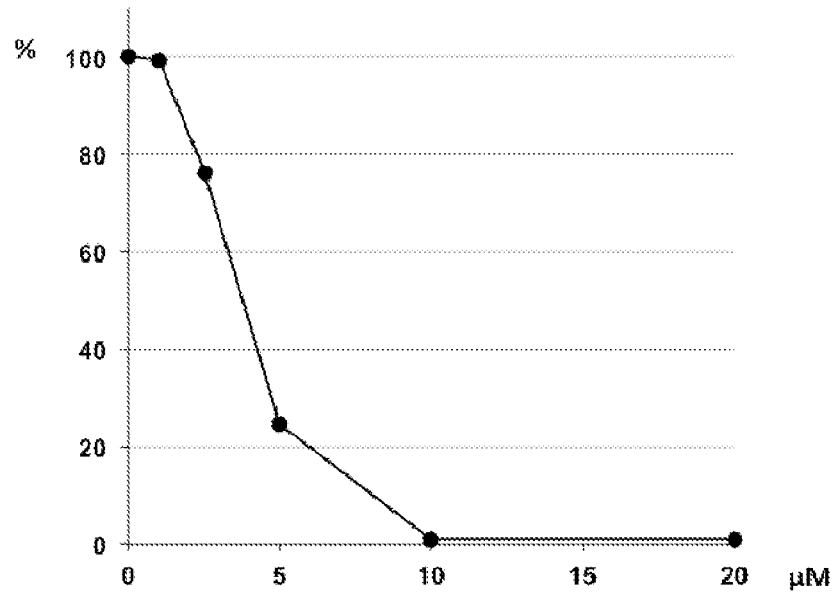
FIG. 8: B-LLC TP53S

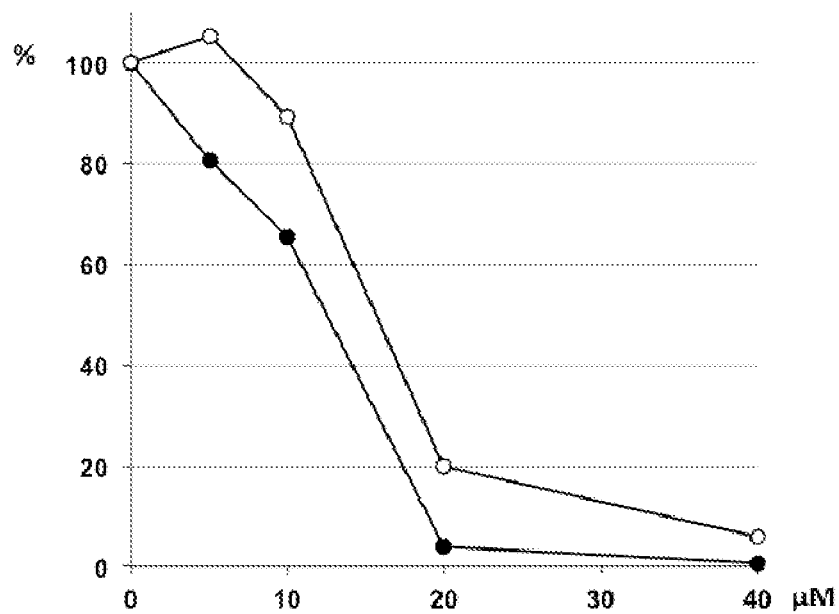
FIG. 9: B y T TP53S
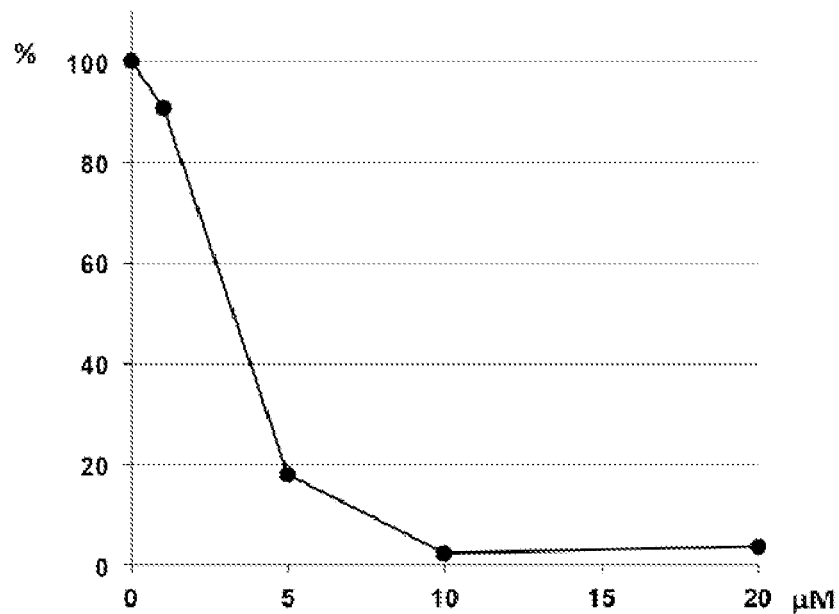
FIG. 10: B-LLC TP53M

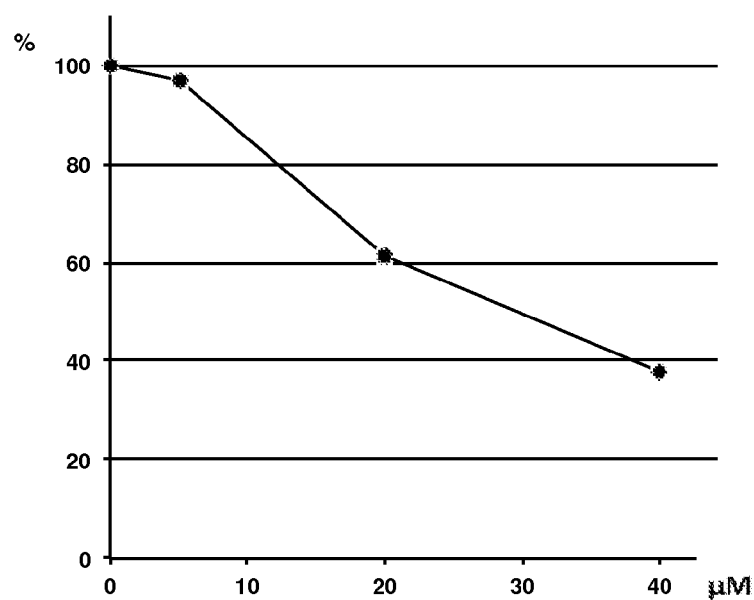
FIG. 11 Jurkat
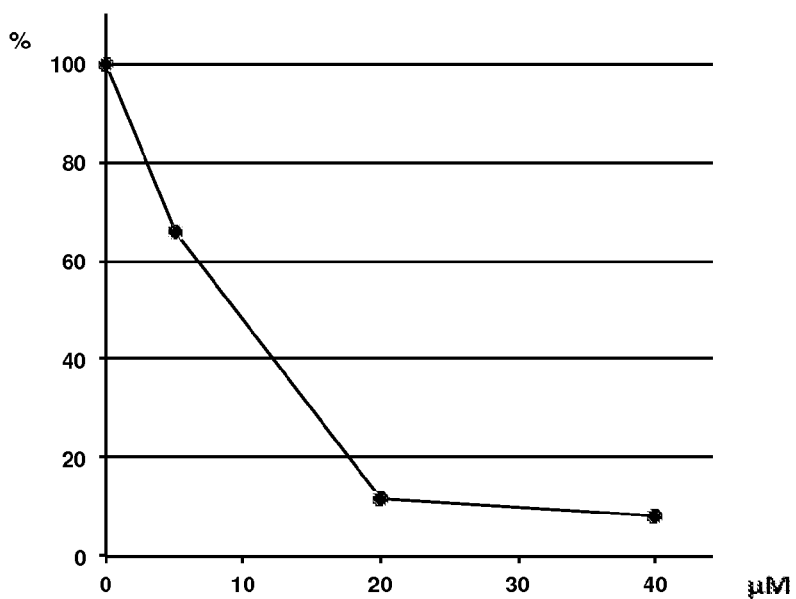
FIG. 12 HeLa

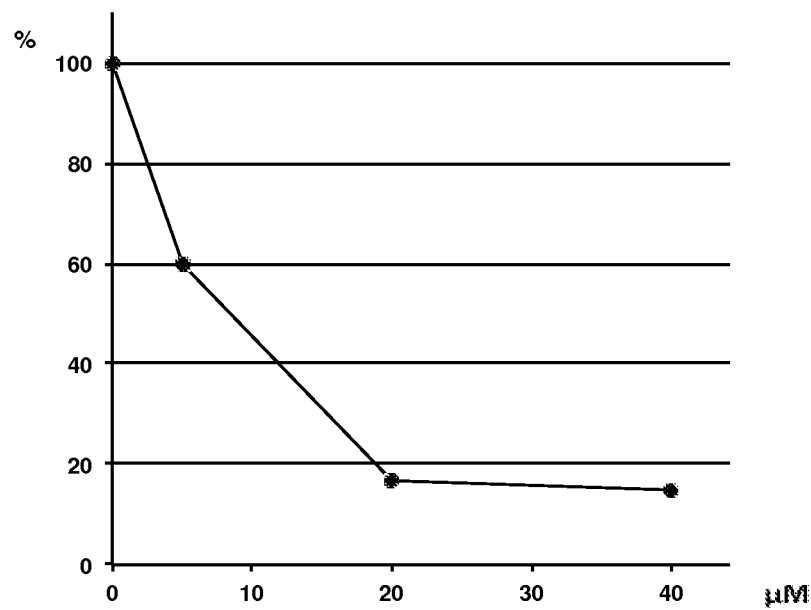
FIG. 13 Jurkat
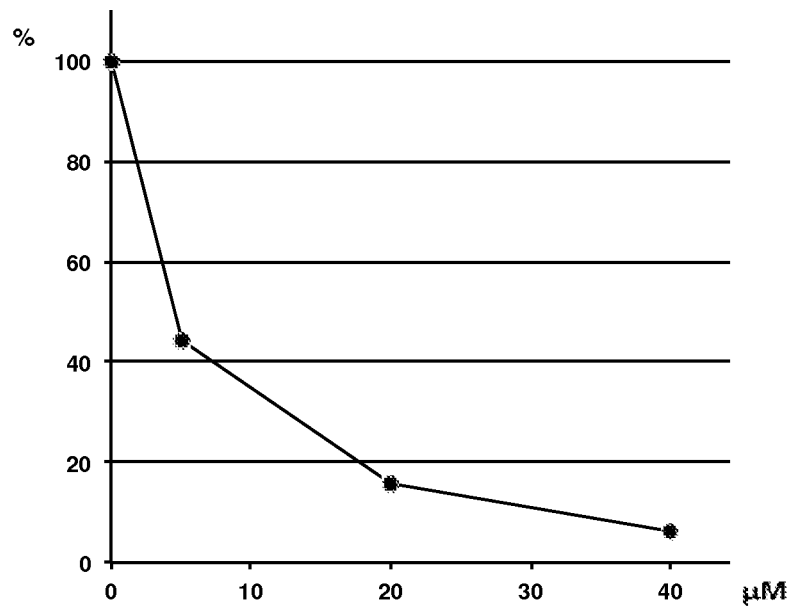
FIG. 14 HeLa

FLUORINATED THIAZOLES FOR USE IN TREATING CANCER

The present invention relates to new thiazole compounds, to pharmaceutical compositions containing them and to their use for the treatment of cancer.

BACKGROUND

Cancer is a heterogeneous disease characterized by the accumulation of tumor cells, which can cause the death of both animals and humans. Conventional methods of treating cancer include surgical treatments, the administration of chemotherapeutic agents, and recently immune response based therapy which involve the administration of an antibody or antibody fragment which may be conjugated to a therapeutic moiety. However, to date, such treatments have been of limited success.

Despite all its limitations, chemotherapy is one of the most extended methods for the treatment of different types of cancer. Thus, the development of new antitumoral therapies of general applicability is one of the main goals in medicinal chemistry.

The incapacity of chemical drugs to distinguish between normal cells that divide rapidly and the tumoral ones, can lead to the patient depression of the immune system. This has been considered one of the main problems of chemotherapy, as well as the mechanisms of resistance developed by cancer cells, which include the inactivation of p53 pathway. Although most drugs currently used in cancer therapy induce apoptosis of these cells, at least partially, through activation of the p53 pathway, p53 protein is mutated in half of all cancers analyzed, demonstrating its importance in cancer development.

Big efforts are being made in the improvement of antitumoral treatments, trying to achieve active and selective compounds that could act independently of p53 pathway, to be given to patients with incipient and recurrent cancer or metastasis.

The presence of thiazole rings is common in many natural bioactive compounds, especially with antitumoral properties. These compounds such as cyclopeptides, polyheterocyclic alkaloids, and compounds of mixed biosynthetic origin display a remarkable structural diversity and often present bis- tris- and 5 polithiazole arrangements. The biosynthetic origin of these substructural units is related to cyclodehydration processes promoted by the thiol of a cysteine and the neighbouring peptide bond. However, the synthetic access to these natural compounds is often complicated, either by peptide-solid phase synthesis, condensation protocols (Hantzsch synthesis) or by means of transition metal couplings from thiazole precursors.

Some bisthiazole compounds with capacity of inhibiting cell proliferation have been described in the art. In WO 2004/016622 some 4,4'-bipyridiyl-2,2'-bisoxazoles and 4,4'-bipyridyl-2,2'-bisthiazoles with antiproliferative activity are described, in particular, against HT-29 cells.

However, despite the research efforts invested in the past, at present there is no curative therapy for most types of cancer, therefore there is still a need to find effective antitumoral agents. In particular, antitumoral therapies which act independently of p53 would be of great interest.

SUMMARY

Found and described here are a new family of thiazoline compounds substituted by fluorine atoms and with a variety of aromatic rings to build tri- and tetra-aromatic rings constructs. These compounds have antitumoral properties (apoptotic properties) against several cancer cell lines, and therefore, are useful for the treatment and/or prevention of cancer.

It has been found that the compounds hereof induce apoptosis in various tumor cell lines independently of p53 protein. Under normal conditions, on sensing DNA damage, protein p53 prevents the cell from replicating by stopping the cell cycle in G1 or interphase promoting the DNA repair. Nevertheless, when DNA damage is too extensive and fail the attempts to repair the DNA this protein induces apoptosis. Any interruption in the regulation of p53 pathway, in its function or in its target genes increases the capacity of tumor growth.

The fact that these compounds induce apoptosis of cancer cells independently of p53 protein, is of high relevance since the resistance of the tumoral cells to current treatments is partly due to its dependency on the p53 pathway.

Therefore, the compounds hereof are very advantageous since they reduce the chemoresistance problems associated with a lot of antitumorals agents, as well as they are active against a big spectrum of tumoral cell lines.

Thus, an aspect of the present invention relates to the provision of a compound of formula (I), or its pharmaceutically acceptable salts, or its stereroisomers or mixture of stereoisomers,

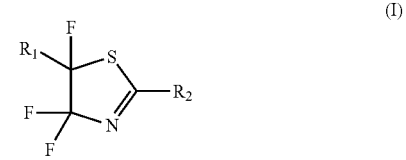

(I)

where: $R_1$ is a radical selected from the group consisting of: phenyl, and phenyl mono-, di-, or tri-substituted by a radical independently selected from the group consisting of F, Cl, Br, I, $(C_1-C_6)$-alkyl, COO—$(C_1-C_6)$-alkyl, and $(C_1-C_6)$-alkoxy; and $R_2$ is a radical selected from the same group as $R_1$, further including a phenyl substituted in 4-position by a radical independently selected from the group consisting of —O(CH$_2$)CONH(CH$_2$)$_3$CH$_3$ and —OCH$_2$COOC(CH$_3$)$_3$, a biphenyl-4-yl, a thiazol-2-yl, and a thiazol-2-yl, mono- or di-substituted, in 4 or 5 positions, by a radical selected from the group consisting of F and phenyl.

The term "biphenyl" means 1,1'-biphenyl.

The term "pharmaceutically acceptable salts" used herein encompasses any salt formed from pharmaceutically acceptable non-toxic acids or bases including inorganic or organic acids or bases. There is no limitation regarding the salts, except that if used for therapeutic purposes, they must be pharmaceutically acceptable.

Compounds referred may have asymmetric centers and, therefore, exist in different enantiomeric forms. All single optical isomers and stereoisomers of the compounds referred to herein, and mixtures thereof, are considered within the scope of the present invention. Thus, any given compound referred to herein is intended to represent any one of a racemate, one or more enantiomeric forms, one or more atropisomeric forms, and mixtures thereof.

Preferably, compounds of formula (I) are those where $R_2$ is a radical selected from the same group as $R_1$, further including a biphenyl-4-yl, a thiazol-2-yl, and a thiazol-2-yl mono- or di-substituted, in 4 or 5 positions, by a radical selected from the group consisting of F and phenyl.

In a preferred implementation, compounds of formula (I) are those where $R_1$ is selected from the group consisting of: phenyl, and phenyl mono-substituted by a radical independently selected from the group consisting of Cl, $(C_1-C_4)$-alkyl, COO—$(C_1-C_4)$-alkyl. In a more preferred implementation, compounds of formula (I) are those where $R_1$ is selected from the group consisting of: phenyl, 4-ethylphenyl, 4-chlorophenyl, 2-methylphenyl, 4-methylphenyl, and 2- or 4-ethoxyphenylcarbonyl.

In another preferred implementation, compounds of formula (I) are those where $R_2$ is a radical selected from the group consisting of: phenyl, and phenyl mono-substituted by a radical independently selected from the group consisting of Cl, $(C_1-C_4)$-alkyl, and COO—$(C_1-C_4)$-alkyl. In a more preferred implementation, compounds of formula (I) are those where $R_2$ is a radical selected from the group consisting of: phenyl, 4-ethylphenyl, 4-chlorophenyl, 2-methylphenyl, 4-methylphenyl, 2-ethoxyphenylcarbonyl, and 4-ethoxyphenylcarbonyl.

In another preferred implementation, compounds of formula (I) are those where $R_2$ is biphenyl-4-yl.

In another preferred implementation, compounds of formula (I) are those where
$R_2$ is selected from a thiazol-2-yl, and a thiazol-2-yl mono- or di-substituted, in 4 or 5 positions, by a radical selected from the group consisting of F and phenyl, having the following formula (Ia):

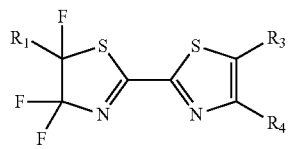

(Ia)

In the previous formula $R_1$ has the same meaning as in compounds of formula (I) and $R_3$ and $R_4$ are independently selected from F and phenyl.

In another preferred implementation, compounds of formula (I) are those where $R_2$ is 5-phenylthiazol-2-yl or 4-fluoro-5-phenylthiazol-2-yl.

In another preferred implementation, compounds of formula (I) are those where $R_2$ is phenyl substituted in 4 position by —O$(CH_2)$CONH$(CH_2)_3CH_3$ or by OCH$_2$COOC$(CH_3)_3$.

The most preferred compounds of formula (I) are those selected from Table 1:

TABLE 1

| Compound (I) | $R_1$ | $R_2$ |
|---|---|---|
| $I_a$ | phenyl | 4-fluoro-5-phenylthiazol-2-yl |
| $I_b$ | phenyl | 5-phenylthiazol-2-yl |
| $I_c$ | phenyl | phenyl |
| $I_d$ | 4-chlorophenyl | 4-chlorophenyl |
| $I_e$ | phenyl | biphenyl-4-yl |
| $I_f$ | 4-methylphenyl | 4-ethoxycarbonylphenyl |

Compounds of the invention may be easily prepared in a flexible manner from commercial reagents by a variety of methods.

Compounds of formula (I) where $R_1$ is equal to $R_2$, $R_1$ and $R_2$ being selected from the group consisting of: phenyl, and phenyl mono-, di-, or tri-substituted by a radical independently selected from the group consisting of F, Cl, Br, I, $(C_1-C_6)$-alkyl, COO—$(C_1-C_6)$-alkyl, and $(C_1-C_6)$-alkoxy can be prepared by a process comprising first submitting a compound of formula (II) where X is an halogen to a Suzuki coupling with a compound of formula $R_1B(OH)_2$, wherein $R_1$ has the same meaning as for compound (I), in the presence of a palladium catalyst, followed by submitting the compound obtained to a fluorination reaction with a fluorinating agent to give a compound of formula (I) with $R_1=R_2$.

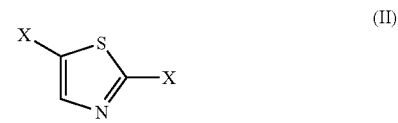

(II)

Preferably, 2,5-dibromothiazole is used as starting material although other 2,5-dihalogenothiazole can also be used as starting materials.

Scheme I illustrates a particular implementation of the process for the preparation of symmetrical compounds of formula (I).

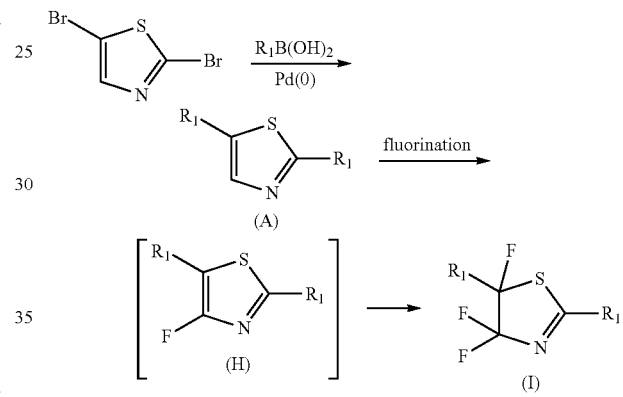

According to the previous scheme, 4,4',5-trifluoro-4,5-dihydrothiazole of formula (I) can be obtained by direct homocoupling of 2,5-dibromothiazole using a palladium catalyst such as Pd(OAc)$_2$, a base such as sodium carbonate and an appropriate solvent such as a $(C_6-C_8)$ aromatic hydrocarbon, for instance, toluene. In general, the reaction is carried out at a temperature of about 90-110° C., preferably about 100° C.

Further fluorination in the thiazole ring of the compound (A) obtained with a fluorinating agent such as 1-chloromethyl-4-fluoro-1,4-diazoniabicyclo[2.2.2]octane bis-(tetrafluoroborate) (Selectfluor®) afford compounds of formula (I) with good yields. The fluorination can be carried out in an appropriate solvent such as acetonitrile, generally at high temperatures, in particular at reflux temperature of the solvent employed.

The fluorination process allows in some occasions to isolate the corresponding monofluorinated compound (H).

Preferably, a compound of formula $R_1B(OH)_2$ where $R_1$ is selected from phenyl, 4-ethylphenyl, 4-methylphenyl, 4-chlorophenyl, and 2-methylphenyl is used.

Compounds of formula (I) with $R_1$ different to $R_2$; where $R_1$ has the same meaning as mentioned above and $R_2$ is a radical selected from the same group as $R_1$, further including biphenyl-4-yl can be prepared by a process comprising first submitting a compound of formula (III) to a Suzuki coupling with a compound of formula $R_2B(OH)_2$ wherein $R_2$ is a radical selected from the same group as $R_1$, further including biphenyl-4-yl, in the presence of a palladium catalyst, then halogenating the compound obtained with an halogen source, subsequently coupling the compound obtained with a compound of formula $R_1B(OH)_2$, wherein $R_1$ has the same meaning as for compound (I), in the presence of a palladium catalyst; and, finally, submitting the compound obtained to a fluorination reaction with a fluorinating agent to give a compound of formula (I) with $R_1$ different from $R_2$.

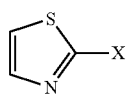

Preferably, 2-bromothiazole is used as starting material, although other 2-halothiazoles can also be used.

Scheme II illustrates a particular implementation of the process of non-symmetrical compounds of formula (I)

Scheme II:

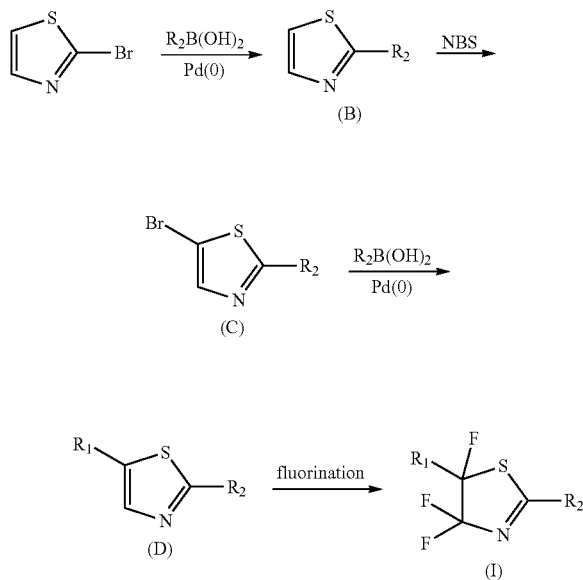

According to the previous scheme, non-symmetrical compounds of formula (I) can be obtained by Suzuki coupling of 2-bromothiazole with a boronic acid of formula $R_2B(OH)_2$ using a palladium catalyst such as $Pd(OAc)_2$, a base such as sodium carbonate and an appropriate solvent such as such as a ($C_6$-$C_8$)— aromatic hydrocarbon, for instance, toluene. In general, the reaction is carried out at a temperature of between about 90-110° C., preferably, at a temperature about 100° C.

The resulting compound of formula (B) can be halogenated at the 5 position. Preferably, the halogenation reaction is a bromination which is carried out with a bromine source like N-bromosuccinimide (NBS), yielding to a compound a formula (C).

Subsequently, a new phenyl group can be introduced in position 5 by Suzuki coupling with a compound of formula $R_1B(OH)_2$ using a palladium catalyst such as $Pd(OAc)_2$, a base such as sodium carbonate and an appropriate solvent such as a ($C_6$-$C_8$) aromatic hydrocarbon, for instance, toluene. In general, the reaction is carried out at a temperature of between about 90-110° C., preferably, at a temperature about 100° C.

Further the fluorination in the thiazole ring of the compound (D) obtained can be carried out as described above, for instance, with a fluorinating agent such as 1-chloromethyl-4-fluoro-1,4-diazoniabicyclo[2.2.2]octane bis-(tetrafluoroborate) (Selectfluor®) to afford compounds of formula (I) in good yields.

Alternatively, compounds of formula (I) with $R_1$ different to $R_2$ as those mentioned above can be prepared by a process comprising first submitting a compound of formula ((III) to a Suzuki coupling with a compound of formula $R_2B(OH)_2$ where $R_2$ is a radical selected from the same group as $R_1$, further including biphenyl-4-yl, where $R_1$ has the same meaning as for compound (I), in the presence of a palladium catalyst, then submitting the compound obtained to a C—H activation reaction with a compound of formula $R_1I$ where $R_1$ has the same meaning as for compound (I); and, finally, submitting the compound obtained to a fluorination reaction with a fluorinating agent to give a compound of formula (I) with $R_1$ different to $R_2$.

In a particular implementation, the compound of formula (I) obtained by this process is that $R_1$ is 4-methylphenyl and $R_2$ is 4-ethoxycarbonylphenyl.

Scheme III illustrates a particular implementation of this process.

Scheme III:

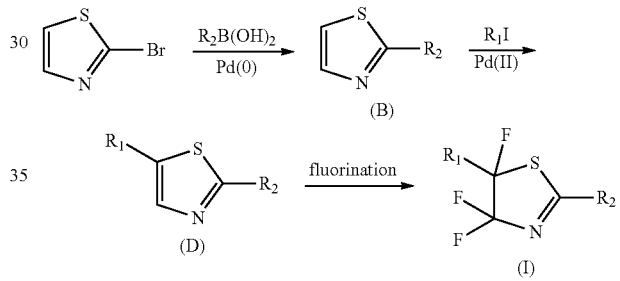

Generally, the Suzuki coupling to yield compound (B) is carried out in the same conditions as mentioned above.

Subsequently, a new aryl group can be introduced in position 5 by a C—H activation reaction with a suitable compound of formula $R_1I$ as defined above using a palladium catalyst such as 1,1'-bis(diphenylphosphine)ferrocene] dichloropalladium(II), and a base such as silver carbonate. The reaction is carried out at a temperature of between about 50 and 70° C., preferably at a temperature about 60° C.

Further fluorination in the thiazole ring of the compound of formula (D) obtained can be carried out as mentioned above.

Finally, compounds of formula (I) where $R_1$ is phenyl and $R_2$ is a thiazol-2-yl substituted by a phenyl can be prepared by a process comprising submitting a compound of formula (III) to a homocoupling reaction in the presence of a palladium catalyst, then halogenating the compound obtained with a halogen source, followed by submitting the compound obtained to a Suzuki coupling with a compound of formula $R_{1a}B(OH)_2$, wherein $R_{1a}$ is phenyl, in the presence of a palladium catalyst, followed by submitting the compound obtained to a fluorination reaction with a fluorinating agent to give a compound of formula (I) where $R_1$ is phenyl and $R_2$ is thiazol-2-yl substituted by a phenyl.

Preferably, the halogenating reaction is a brominating reaction.

Scheme (IV) illustrates a particular implementation of the process.

Scheme IV:

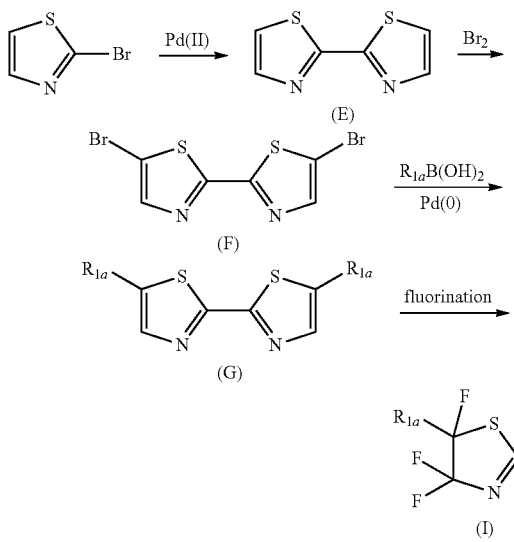

According to the previous scheme, 4,4',5-trifluoro-4,5-dihydrothiazole of formula (I) can be obtained by homocoupling of 2-bromothiazole using a palladium catalyst such as Pd(OAc)$_2$, a base such as diisopropylethylamine and an appropriate solvent such as toluene. The 2,2'-bisthiazole obtained of formula (E) can be halogenated with a halogen source, such as a bromide source, for instance, bromine to furnish the 5,5'-dibromo-2,2'-bisthiazole of formula (F).

Subsequently, a Suzuki coupling reaction is carried out with a boronic acid of formula $R_{1a}B(OH)_2$ using a palladium catalyst such as tetrakis(triphenylphosphine)palladium(0), a base such as sodium carbonate and an appropriate solvent such as toluene, in the same preferred conditions as those mentioned above for carrying out the Suzuki coupling.

Further fluorination of the compound of formula (G) previously obtained using a fluorinating agent such as 1-chloromethyl-4-fluoro-1,4-diazoniabicyclo[2.2.2]octane bis-(tetrafluoroborate) (Selectfluor®) is carried out in the conditions previously described.

The preparation processes described above can be modified to give enantiopure compounds as well as mixtures of stereoisomers. It is possible to prepare specific stereoisomers or specific mixtures by various processes including the use of stereospecific reagents or by introducing chiral centers into the compounds during the preparation process. In addition, it is possible to separate stereoisomers once the compound has been prepared by standard resolution techniques known to the skilled person.

The preparation of pharmaceutically acceptable salts of the compounds of formula (I) can be carried out by methods known in the art. For instance, they can be prepared from the parent compound, which contains a basic or acidic moiety, by conventional chemical methods. Generally, such salts are, for example, prepared by reacting the free acid or base forms of these compounds with a stoichiometric amount of the appropriate pharmaceutically acceptable base or acid in water or in an organic solvent or in a mixture of them.

The compounds of the invention may be in crystalline form either as free solvation compounds or as solvates (e.g. hydrates) and it is intended that both forms are within the scope of the present invention. Methods of solvation are generally known within the art.

An important feature of the compounds hereof may include their bioactivity inhibiting cell growth of the tested tumor cell lines and in particular their cytotoxic activity promoting apoptosis. As it is illustrated in the Examples, the compounds hereof show antitumoral properties in several cancer cell lines and in primary chronic lymphocytic leukemia cells.

Thus, another aspect of the present compounds relates to the provision of compounds of formula (I), or their pharmaceutically acceptable salts, or their stereoisomers or mixture of stereoisomers for use as a medicament.

Another aspect of the present compounds relates to the provision of compounds of formula (I), or their pharmaceutically acceptable salts, or their stereoisomers or mixture of stereoisomers for use in the treatment and/or prevention of cancer as they are active in all the types of cancer where have been tested.

In a particular implementation, provided are the compounds of formula (I), or their pharmaceutically acceptable salts, or their stereoisomers or mixture of stereoisomers for use in the treatment and/or prevention of tumors with mutated TP53.

Preferably, the compounds hereof are especially active against the following types of cancer: leukemia, lymphoma, cervical carcinoma, breast adenocarcinoma, glioblastoma and hepatocellular carcinoma. More preferably, the cancer is leukemia or lymphoma. Even more preferably, the type of lymphoma or of the leukemia is B-cell neoplasms.

This aspect can also be formulated as the use of compounds of formula (I) as defined above for the preparation of a medicament for the treatment and/or prevention of a cancer in a mammal, including a human.

The invention also relates to a method of treatment of a mammal, including a human, suffering from or being susceptible of suffering from cancer, in particular to one of the cancers mentioned above, said method comprising the administration to said patient of a therapeutically effective amount of a compound of formula (I) as defined above, together with pharmaceutically acceptable excipients or carriers.

Compounds hereof can be used in the same manner as other known chemotherapeutic agents. They may be used alone or in combination with other suitable bioactive compounds.

A further aspect hereof relates to a pharmaceutical composition comprising a therapeutically effective amount of the compounds hereof, together with appropriate amounts of pharmaceutically acceptable excipients or carriers.

The expression "therapeutically effective amount" as used herein, refers to the amount of a compound that, when administered, is sufficient to prevent development of, or alleviate to some extent, one or more of the symptoms of the disease which is addressed. The particular dose of compound administered according to this disclosure will of course be determined by the particular circumstances surrounding the case, including the compound administered, the route of administration, the particular condition being treated, and the similar considerations.

The expression "pharmaceutically acceptable excipients or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio.

The chemotherapeutic treatment of cancer that derives from this disclosure may yield a novel approach to cancer therapy and has the advantageous feature of being useful for the treatment of several types of cancer.

Throughout the description and claims the word "comprise" and variations of the word, are not intended to exclude other technical features, additives, components, or steps. Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

BRIEF DESCRIPTION OF THE DRAWINGS

FIG. 1 shows the dose-response of compound $I_a$ from 1 μM to 10 μM in Jurkat cell line (T lymphocytes from acute T cell leukemia, with mutated TP53) at 24 hours of culture. Viability was measured by flow cytometry and it is expressed as the percentage of nonapoptotic cells (annexin-V APC negative).

FIG. 2 shows the dose-response of compound $I_a$ from 2 μM to 40 μM in HeLa cells (epithelial cervical carcinoma cell line with inactivated p53) at 24 hours of culture. Viability was measured by flow cytometry and it is expressed as the percentage of nonapoptotic cells (annexin-V APC negative).

FIG. 3 shows the dose-response of compound $I_a$ from 2 μM to 40 μM in TK6 cells (human lymphoblast cell line with wild-type TP53) at 24 hours of culture. Viability was measured by flow cytometry and it is expressed as the percentage of nonapoptotic cells (annexin-V APC negative).

FIG. 4 shows the dose-response of compound $I_a$ from 2 μM to 40 μM in Ramos cell line (B lymphocytes from Burkitt's lymphoma with mutated TP53) at 24 hours of culture. Viability was measured by flow cytometry and it is expressed as the percentage of nonapoptotic cells (annexin-V APC negative).

FIG. 5 shows the dose-response of compound $I_a$ from 2 μM to 60 μM in MDA-MB-231 cells (epithelial breast adenocarcinoma cell line with mutated TP53) at 24 hours of culture. Viability was measured by flow cytometry and it is expressed as the percentage of nonapoptotic cells (annexin-V APC negative).

FIG. 6 shows the dose-response of compound $I_a$ from 2 μM to 60 μM in T98-G cells (glioblastoma cell line with mutated TP53) at 24 hours of culture. Viability was measured by flow cytometry and it is expressed as the percentage of nonapoptotic cells (annexin-V APC negative).

FIG. 7 shows the dose-response of compound $I_a$ from 2 μM to 40 μM in Hep3B cell line (Epithelial, well-differentiated, hepatocellular carcinoma cell line with deleted TP53) at 24 hours of culture. Viability was measured by crystal violet assay and it is expressed as the percentage of viable cells relative to control cells.

FIG. 8 shows the dose-response of compound $I_a$ from 1 μM to 20 μM in wild-type TP53 B cells from Chronic Lymphocytic Leukemia patients (CLL), (B-CLL p53WT) at 24 hours of culture. Viability was measured by flow cytometry and it is expressed as the percentage of nonapoptotic cells (annexin-V APC negative). A representative patient is shown.

FIG. 9 shows the dose-response of compound $I_c$ from 5 μM to 40 μM in wild-type TP53 CLL cells, B cells (black dots) and T cells (open dots) (B and T p53WT) at 24 hours of culture. Viability was measured by flow cytometry and it is expressed as the percentage of nonapoptotic cells (annexin-V FITC negative). A representative patient is shown.

FIG. 10 shows the dose-response of compound $I_a$ from 1 μM to 20 μM in mutated TP53 CLL cells (B-CLL p53M) at 24 hours of culture. Viability was measured by flow cytometry and it is expressed as the percentage of nonapoptotic cells (annexin-V APC negative). A representative patient is shown.

FIG. 11 shows the dose-response of compound $I_g$ from 5 μM to 40 μM in Jurkat cell line (T lymphocytes from acute T cell leukemia, with mutated TP53) at 24 hours of culture. Viability was measured by flow cytometry and it is expressed as the percentage of nonapoptotic cells (annexin-V APC negative).

FIG. 12 shows the dose-response of compound $I_g$ from 5 μM to 40 μM in HeLa cells (epithelial cervical carcinoma cell line with inactivated TP53) at 24 hours of culture. Viability was measured by flow cytometry and it is expressed as the percentage of nonapoptotic cells (annexin-V APC negative).

FIG. 13 shows the dose-response of compound $I_h$ from 5 μM to 40 μM in Jurkat cell line (T lymphocytes from acute T cell leukemia, with mutated TP53) at 24 hours of culture. Viability was measured by flow cytometry and it is expressed as the percentage of nonapoptotic cells (annexin-V APC negative).

FIG. 14 shows the dose-response of compound $I_h$ from 5 μM to 40 μM in HeLa cells (epithelial cervical carcinoma cell line with inactivated TP53) at 24 hours of culture. Viability was measured by flow cytometry and it is expressed as the percentage of nonapoptotic cells (annexin-V APC negative).

EXAMPLES

Unless stated otherwise, all reactions were carried out under argon atmosphere in dried glassware. Commercially available reactants were used without further purification. Reaction temperatures were controlled by an IKA temperature modulator. Thin-layer chromatography was conducted with Merck silica gel 60 F254 sheets and visualized via UV, and $KMnO_4$ solutions. Silica gel (particle size 35-70 μm) was used for flash column chromatography. HPLC reversed-phase columns Symmetry C18 4.6 mm×150 mm, 5 μm (column A) were used. Analytical HPLC was performed on an instrument having two solvent delivery pumps, automatic injector dual wavelength detector, and system controller (Breeze V3.20) and on an instrument having two solvent delivery pumps, automatic injector, and a variable wavelength detector (photodiode array). MALDI-TOF analysis of examples was performed using ACH matrix. IR spectra were recorded on a Thermo Nicolet Nexus spectrometer and are reported in frequency of absorption (cm-1). Melting Point was performed on Büchi Melting Point B-540.

Example 1

Preparation of 2,2'-bisthiazole (compound E)

An oven-dried round-bottomed flash and condenser were placed under a nitrogen atmosphere and charged with 2-bromothiazole (12.88 g, 78.53 mmol), N,N-diisopropylethylamine (13.8 mL, 78.80 mmol), palladium acetate (0.90 g, 3.93 mmol) and tetrabutylamonium bromide (12.67 g, 39.30 mmol). The flask was evacuated and re-filled with nitrogen three times, and then toluene (170 mL) was added. The reaction mixture was heated at 105° C. for 24 h. When the reaction was completed, $H_2O$ (150 mL) was added and the mixture extracted with dichloromethane (DCM) (3×50 mL). The organic extracts were dried over $Na_2SO_4$, filtered, and evaporated in vacuo. Flash chromatography of the residue on silica gel ($SiO_2$, hexane:ethyl acetate, 9:1) afforded 8.20 g of 2,2'-bisthiazole as a yellow solid (63% yield). $^1$H-RMN ($CDCl_3$, 400 MHz): δ 7.90; (d, J=3.1 Hz, 2H), 7.44; (d, J=3.1 Hz, 2H) ppm. EM (IE): m/z (%): 168 (M+, 100).

Example 2

Preparation of 5,5'-dibromo-2,2'-bisthiazole (compound F)

To a solution of 2,2'-bisthiazol (84 mg, 0.5 mmol) in anhydrous dichloromethane (DCM) (5 mL) was slowly added $Br_2$ (103 mL, 2 mmol). The reaction was stirred for 10 h at room temperature. Then was added $NaHCO_3$ (21 mg, 0.25 mmol) and the mixture was stirred for 38 h. When the reaction was completed, it was diluted with DCM (25 mL) and washed with an aqueous solution of $NaHCO_3$ (4×50 mL) with $H_2O$ (4×50 mL) and $Na_2SO_3$ (4×50 mL). The organic extracts were dried over $Na_2SO_4$, filtered and evaporated under reduced pressure. Flash chromatography of the residue on silica gel ($SiO_2$, hexane:ethyl acetate, 1:1) afforded 138 mg of 5,5'-dibromo-2,2'-bisthiazole as a brown solid (85% yield). $^1$H-RMN ($CDCl_3$, 400 MHz): δ7.75; (s, 2H) ppm. $^{13}$C-RMN ($CDCl_3$, 400 MHz): δ 161.91, 145.12, 112.03 ppm. IR (NaCl): v1695, 1468, 1142, 1132, 998, 918, 899, 850, 745, 631, 604, 474 cm-1. UV-Vis. [$\lambda_{max}$ nm (log ε), MeOH]: 341.50; (4.43). EM (IE): m/z (%): 326; (M+, 100), 167; (76.13), 83; (4.47), 57; (47.51).

Example 3

Preparation of 5,5'-diphenyl-2,2'-bisthiazole (compound G)

An oven-dried round-bottomed flash and condenser were placed under a nitrogen atmosphere and charged with 5,5'-dibromo-2,2'-bisthiazole (440 mg, 1.35 mmol), and tetrakis(triphenylphosphine)palladium (0) (94.4 mg, 0.081 mmol). The flask was evacuated and re-filled with nitrogen three times and then toluene (170 mL) was added. To the solution was added with stirring an aqueous solution of $Na_2CO_3$ 2 M (5.4 mL) and phenylboronic acid (373.2 mg, 2.97 mmol). The reaction mixture was heated to 80° C. for 12 h. When the reaction was completed, inorganic solids were removed by filtration through Celite® and washing with several portions of dichloromethane, then the solvent was evaporated. The residue was absorbed onto silica then subjected to flash chromatography ($SiO_2$, hexane: ethyl acetate (AcOEt), 8:2). After crystallization with toluene gave 5,5'-diphenyl-2,2'-bisthiazole as yellow solid (82% yield). $^1$H-RMN (CDCl3, 400 MHz): δ 8.06; (s, 2H), 7.63; (m, 4H), 7.45; (m, 4H), 7.38; (m, 2H) ppm. $^{13}$C-RMN ($CDCl_3$, 400 MHz): δ 160.2, 141.4, 139.4, 130.9, 129.3, 128.9, 126.8 ppm. IR (NaCl): v3064, 1477, 1442, 1394, 1332 cm-1. UV-Vis. [$\lambda_{max}$ nm (log ε), MeOH]: 377.50; (4.43), 254.00; (4.05), 201.00; (4.60). Melting point: 237.4-239.0° C. EM (IE): m/z (%): 320; (M+, 100). HRMS (ESI): calculated for $C_{18}H_{13}N_2S_2$: 321.0515. found: 321.0518.

Example 4

Preparation of 4-fluoro-5-phenyl-2-(4,4,5-trifluoro-5-phenyl-4,5-dihydrothiazol-2-yl)thiazole (compound (I) with $R_1$=phenyl and $R_2$=4-fluoro-5-phenylthiazol-2-yl, compound ($I_a$))

To a solution of 5,5'-diphenyl-2,2'-bisthiazole (100 mg, 0.31 mmol) in acetonitrile (can) (8 mL) was added Selectfluor® (232.8 mg, 0.62 mmol). The reaction was stirred for 12 h at reflux temperature. After this time, again was added more Selectfluor® (232.8 mg, 0.62 mmol) and the mixture was stirred for 12 h at reflux temperature. Then diluted with diethyl ether (50 mL) and washed with $H_2O$ (3×25 mL) and saturated aqueous $NaHCO_3$ (3×25 mL). The organic extracts were dried over $Na_2SO_4$, filtered and evaporated under reduced pressure The residue was absorbed onto silica then subjected to flash chromatography ($SiO_2$, hexane:AcOEt, 8:2), obtaining 10 mg of 4-fluoro-5-phenyl-2-(4,4,5-trifluoro-5-phenyl-4,5-dihydrothiazol-2-yl)thiazole as a white solid (22% yield). $^1$H-RMN ($CDCl_3$, 400 MHz): δ 7.70; (m, 4H), 7.48; (m, 6H) ppm. $^{19}$F-RMN ($CDCl_3$, 400 MHz): δ −79.98; (dd, J=219.06, 9.07 Hz), −103.63; (s), −103.73; (dd, J=219.05, 7.85 Hz), −131.52; (m) ppm. EM (IE): m/z (%): 395.02; (M+, 100). HRMS (ESI): calculated for $C_{18}H_{10}F_4N_2S_2$: 395.0294; found: 395.0285.

Example 5

Preparation of 5-phenyl-2-(4,4,5-trifluoro-5-phenyl-4,5-dihydrothiazol-2-yl)thiazole ((compound (I) with $R_1$=phenyl and $R_2$=5-phenylthiazol-2-yl, compound ($I_b$))

The compound of the title was prepared in a similar way to Example 4 from 5,5'-diphenyl-2,2'-bisthiazole (100 mg, 0.31 mmol) and Selectfluor® (465.6 mg, 1.24 mmol), obtaining 20 mg of a white solid (27% yield). $^1$H-RMN ($CDCl_3$, 400 MHz): δ 8.24; (s, 1H), 7.72; (m, 2H), 7.66; (m, 2H), 7.49; (m, 6H) ppm. $^{19}$F-RMN ($CDCl_3$, 400 MHz): δ −79.65 (dd, J=218.74, 9.14 Hz), −103.39 (dd, J=218.73, 7.89 Hz), −131.58 (m) ppm. EM (IE): m/z (%): 377.03 (M+, 100).

Example 6

Preparation of 2,5-diphenythiazol (compound A with $R_1$=phenyl, ($A_c$))

The compound of the title was prepared in a similar way to Example 3 from 2,5-dibromothiazole (200 mg, 0.80 mmol) and phenylboronic acid (220.8 mg, 1.76 mmol) for 18 h at 80° C. The residue was absorbed onto silica then subjected to flash chromatography ($SiO_2$, hexane:AcOEt, 9:1), obtaining 78 mg of 2,5-dibromothiazole as a yellow solid (42% yield). EM (IE): m/z (%): 237.89; (M+, 100). HRMS (ESI): calculated for $C_{15}H_{11}$ NS: 238.0685. found: 238.0685

Example 7

Preparation of 2,5-bis(4-ethylphenyl)thiazole (compound A with $R_1$=4-ethylphenyl, compound ($A_h$))

The compound of the title was prepared in a similar way to Example 3 from 2,5-dibromothiazole (250 mg, 1.00 mmol) and acid 4-ethylphenylboronic (339.6 mg, 2.20 mmol) for 3 h at 100° C. The residue was absorbed onto silica then subjected to flash chromatography ($SiO_2$, hexane:AcOEt, 9:1), obtaining 242 mg of 2,5-bis(4-ethylphenyl)thiazole as a yellow solid (83% yield). EM (IE): m/z (%): 293; (M+, 100). HRMS (ESI): (M+H)+ calculated for $C_6H_3N_2S_2I_2$: 294.1311; found: 294.1313.

Example 8

Preparation of 2,5-bis(4-chlorophenyl)thiazole (compound A with $R_1$=4-chlorophenyl, compound ($A_d$))

The compound of the title was prepared in a similar way to Example 3 from 2,5-dibromothiazole (250 mg, 1.00 mmol)

and acid 4-chlorophenylboronic (361.5 mg, 2.20 mmol) for 3 h at 100° C. The residue was absorbed onto silica then subjected to flash chromatography (SiO$_2$, hexane:AcOEt, 9:1), obtaining 236 mg of 2,5-bis(4-chlorophenyl)thiazole as a white solid (78% yield). EM (IE): m/z (%): 305.9 (M+, 100). 307.9; (M+, 69). HRMS (ESI): calculated for C$_{15}$H$_9$Cl$_2$NS: 304.9906. found: 304.9902.

Example 9

Preparation of 2,5-di-o-tolylthiazole (compound A with R$_1$=2-methylphenyl, compound (A$_i$))

The compound of the title was prepared in a similar way to Example 3 from 2,5-dibromothiazole (264 mg, 1.08 mmol) and acid o-tolylphenylboronic (325.0 mg, 2.39 mmol) for 3 h at 100° C. The residue was absorbed onto silica then subjected to flash chromatography (SiO$_2$, hexane:AcOEt, 8:2), obtaining 218 mg of 2,5-di-o-tolylthiazole as a yellow solid (74% yield). HRMS (ESI): calculated for C$_{17}$H$_{16}$NS: 266.0998. found: 266.1005.

Example 10

Preparation of 2,5-di-p-tolylthiazole (compound A with R$_1$=4-methylphenyl, compound (A$_g$))

The compound of the title was prepared in a similar way to Example 3 from 2,5-dibromothiazole (250 mg, 1.00 mmol) and acid p-tolylphenylboronic (317.3 mg, 2.20 mmol) for 3 h at 100° C. The residue was absorbed onto silica then subjected to flash chromatography (SiO$_2$, hexane:AcOEt, 8:2), obtaining 202 mg of 2,5-di-p-tolylthiazole as a yellow solid (73% yield) EM (IE): m/z (%): 265.1; (M+, 100). HRMS (ESI): calculated for C$_{17}$H$_{16}$NS: 266.0998. found: 266.0999.

Example 11

Preparation of 4,4,5-trifluoro-2,5-diphenyl-4,5-dihydrothiazole (compound (I) with R$_1$=R$_2$=phenyl, compound (I$_c$))

The compound of the title was prepared in a similar way to Example 4 from 2,5-diphenylthiazole (50 mg, 0.18 mmol) and Selectfluor® (164.1 mg, 0.44 mmol) in ACN for 2 h at 80° C. The residue was absorbed onto silica then subjected to flash chromatography (SiO$_2$, hexane:AcOEt, 9:1), obtaining 15 mg of 4,4,5-trifluoro-2,5-diphenyl-4,5-dihydrothiazole as a white solid (28% yield). $^1$H-NMR (CDCl$_3$, 400 MHz): δ 8.04-7.98 (m, 2H), 7.74-7.60; (m, 2H), 7.56-7.52; (m, 2H), 7.50-7.41; (m, 4H) ppm. $^{19}$F-NMR (CDCl$_3$, 400 MHz): δ −79.76; (dd, J=218.04, 10.26 Hz), −103.77; (dd, J=218.14, 8.32 Hz), −130.96 (m) ppm. HRMS (ESI): calculated for C$_{15}$H$_{10}$F$_3$NS: 293.0486. found: 293.0553.

Example 12

Preparation of 4,4,5-trifluoro-2,5-bis(4-ethylphenyl)-4,5-dihydrothiazole (compound (I) with R$_1$=R$_2$=4-ethylphenyl, compound (I$_h$))

The compound of the title was prepared in a similar way to Example 4 from 2,5-bis(4-ethylphenyl)thiazole (100 mg, 0.34 mmol) and Selectfluor® (305.0 mg, 0.82 mmol) in ACN for 1 h at 80° C. The residue was absorbed onto silica then subjected to flash chromatography (SiO$_2$, hexane:AcOEt, 9:1), obtaining 21 mg of 4,4,5-trifluoro-2,5-bis(4-ethylphenyl)-4,5-dihydrothiazole as a white solid (18% yield). $^1$H-RMN (CDCl$_3$, 400 MHz): δ 7.92; (d, J=8.24 Hz, 2H), 7.62; (d, J=7.96 Hz, 2H), 7.32; (dd, J=21.08, 8.18 Hz, 4H), 2.73; (qd, J=15.20, 7.59, 7.59, 7.57 Hz, 4H), 1.28; (td, J=7.63, 3.81, 3.81 Hz, 6H) ppm. $^{19}$F-RMN (CDCl3, 400 MHz): δ −79.43; (dd, J=217.43, 9.85 Hz), −103.79; (dd, J=217.38, 9.14 Hz), −130.03; (m) ppm. HRMS (ESI): calculated for C$_{19}$H$_{18}$F$_3$NS: 377.0316. found: 377.0385.

Example 13

Preparation of 4,4,5-trifluoro-2,5-bis(4-chlorophenyl)-4,5-dihydrothiazole (compound (I) with R$_1$=R$_2$=4-chlorophenyl compound (I$_d$))

The compound of the title was prepared in a similar way to Example 4 from 2,5-bis(4-chlorophenyl)thiazole (200 mg, 0.65 mmol) and Selectfluor® (584.5 mg, 1.57 mmol) in ACN for 3 h at 80° C. The residue was absorbed onto silica then subjected to flash chromatography (SiO$_2$, hexane:AcOEt, 95:5), obtaining 47 mg of 4,4,5-trifluoro-2,5-bis(4-chlorophenyl)-4,5-dihydrothiazole as a white solid (21% yield). $^1$H-RMN (CDCl$_3$, 400 MHz): δ 7.94-7.92 (m, 2H), 7.6; (d, J=8.1 Hz, 2H), 7.50-7.53; (m, 2H), 7.44-7.46; (d, J=8.5 Hz, 2H) ppm. $^{19}$F-RMN (CDCl3, 400 MHz): δ−79.70; (dd, J=218.48, 9.93 Hz), −103.70; (dd, J=218.44, 8.20 Hz), −131.38; (m) ppm. EM (IE): m/z (%): 361.1; (M+, 100). 363.1; (M+, 69.4), 362.1; (M+, 18.4), 365.0; (M+, 14.1), 364.1; (M+, 12.1). HRMS (ESI): calculated for C$_{15}$H$_8$Cl$_2$F$_3$NS: 360.9707. found: 360.9782.

Example 14

Preparation of 4,4,5-trifluoro-2,5-di(o-tolyl)-4,5-dihydrothiazole (compound (I) with R$_1$=R$_2$=2-methylphenyl, compound (I$_i$))

The compound of the title was prepared in a similar way to Example 4 from 2,5-di-o-tolylthiazole (197 mg, 0.74 mmol) and Selectfluor® (632.0 mg, 1.78 mmol) in ACN for 5 h at 80° C. The residue was absorbed onto silica then subjected to flash chromatography (SiO$_2$, hexane:AcOEt, 95:5), obtaining 78 mg of 4,4,5-trifluoro-2,5-di-(o-tolyl)-4,5-dihydrothiazole as a white solid (33% yield). $^1$H-RMN (CDCl$_3$, 400 MHz): δ 7.79; (d, 1H), 7.72; (d, 2H), 7.48; (m, 1H), 7.33; (m, 4H), 7.23; (m, 1H), 2.69; (s, 3H), 2.61; (d, 3H) ppm. $^{19}$F-RMN (CDCl$_3$, 400 MHz): δ −78.41; (dd, J=218.81, 8.88 Hz), −97.51; (dd, J=218.85, 10.69 Hz), −126.87; (m) ppm. HRMS (ESI): (M+H)+: calculated for C$_{17}$H$_{15}$F$_3$NS: 322.0872. found: 322.0874.

Example 15

Preparation of 4,4,5-trifluoro-2,5-di-(p-tolyl)-4,5-dihydrothiazole (compound (I) with R$_1$=R$_2$=4-methylphenyl, compound (I$_g$))

The compound of the title was prepared in a similar way to Example 4 from 2,5-di-p-tolylthiazole (100 mg, 0.36 mmol) and Selectfluor® (304.4 mg, 0.86 mmol) in ACN for 10 h at 80° C. The residue was purified by semi-preparative HPLC, obtaining 35 mg of 4,4,5-trifluoro-2,5-di-(p-tolyl)-4,5-dihydrothiazole as a white solid (30% yield). $^1$H-RMN (CDCl$_3$, 400 MHz): δ 7.89; (d, J=8.2 Hz, 2H), 7.60; (d, J=8.0 Hz, 2H), 7.37-7.27; (m, 4H), 2.46; (s, 3H), 2.41; (s, 3H). $^{19}$F-RMN (CDCl$_3$, 400 MHz): δ −79.39; (dd, J=217.6, 9.7

Hz), −102.69; (dd), −130.08; (m). HRMS (ESI): (M+H)+: calculated for $C_{17}H_{15}F_3NS$: 322.0872. found: 322.0871.

Example 16

Preparation of 2-(biphenyl-4-yl)thiazole (compound B with $R_2$=biphenyl-4-yl compound ($B_e$))

The compound of the title was prepared in a similar way to Example 3 from 2-dibromothiazole (500 µL, 5.61 mmol) and acid biphenylboronic (1.22 g, 6.17 mmol) for 12 h at 80° C. The residue was absorbed onto silica then subjected to flash chromatography ($SiO_2$, hexane:AcOEt, 9:1), obtaining 675 mg of 2-(biphenyl-4-yl)thiazole as a white solid (51% yield). EM (IE): m/z (%): 237; (M+, 100). HRMS (ESI): (M+H)+ calculated for $C_{15}H_{11}NS$: 238.0612. found: 238.0683.

Example 17

Preparation of 2-(biphenyl-4-yl)-5-bromothiazole (compound C with $R_2$=biphenyl-4-yl, compound ($C_e$))

To a solution of 2-(biphenyl-4-yl)thiazole (540 mg, 2.28 mmol) in anhydrous acetonitrile (10 mL) was added a solution of N-bromosuccinimide in anhydrous acetonitrile (10 mL). The reaction was stirred for 20 h at room temperature. Subsequently, an aqueous solution of $Na_2SO_3$ 10% (10 ml) was added and the mixture was stirred for 10 minutes. Then, extracted with ethyl acetate (4×25 mL) and the organic layers were washed with an aqueous saturated solution of NaCl (4×50 ml), dried over $Na_2SO_4$, filtered and evaporated under reduced pressure. Flash chromatography of the residue on silica gel (SiO2, hexane:ethyl acetate, 9:1) afforded 500 mg of 2-(biphenyl-4-yl)-5-bromothiazole as a white solid (69% yield). EM (IE): m/z (%): 317; (M+, 100), 315; (M+, 95), 316; (M+, 17.1). HRMS (ESI): (M+H)+: calculated for $C_{15}H_{10}BrNS$: 315.9717. found: 315.9786.

Example 18

Preparation of 2-(biphenyl-4-yl)-5-phenylthiazole (compound D with $R_1$=phenyl and $R_2$=biphenyl-4-yl, compound ($D_e$))

The compound of the title was prepared in a similar way to example 3 from 2-(biphenyl-4-yl)-5-bromothiazole (311 mg, 0.98 mmol) and phenylboronic acid (955 mg, 1.27 mmol) for 4 h at 100° C. Flash chromatography of the residue on silica gel ($SiO_2$, hexane:ethyl acetate, 8:2) afforded 300 mg of 2-(biphenyl-4-yl)-5-phenylthiazole as a white solid (98% yield). EM (IE): m/z (%): 313; (M+, 100). HRMS (ESI): (M+H)+: calculated for $C_{21}H_{15}NS$: 314.0925. found: 314.0995.

Example 19

Preparation of 4,4,5-trifluoro-2-(biphenyl-4-yl)-5-phenyl-4,5-dihydrothiazole thiazole (compound (I) with $R_1$=phenyl and $R_2$=biphenyl-4-yl, compound ($I_e$))

The compound of the title was prepared in a similar way to example 4 from 2-(biphenyl-4-yl)-5-phenylthiazole (150 mg, 0.48 mmol) and Selectfluor® (429 mg, 1.15 mmol) in ACN for 4.5 h at 80° C. Flash chromatography of the residue on silica gel (SiO2, hexane:ethyl acetate, 95:5) afforded 14 mg of 4,4,5-trifluoro-2-(biphenyl-4-yl)-5-phenyl-4,5-dihydrothiazole as a white solid (8% yield). $^1$H-RMN (CDCl$_3$, 400 MHz): δ 8.11-8.04; (m, 2H), 7.78-7.70; (m, 4H), 7.68-7.63; (m, 2H), 7.53-7.40; (m, 6H). $^{19}$F-RMN (CDCl3, 400 MHz): δ −79.45; (dd, J=218.0, 10.0 Hz), −103.63; (dd, J=217.9, 8.7 Hz), −130.77; (m). HRMS (ESI): (M+H)+: calculated for $C_{21}H_{14}F_3NS$: 370.0872. found: 370.0868.

Example 20

Preparation of ethyl 4-(thiazole-2-yl)benzoate (compound B with $R_2$=4-ethoxycarbonylphenyl. compound ($B_f$))

The compound of the title was prepared in a similar way to example 3 from 2-dibromothiazole (200 µL, 2.24 mmol) and 4-ethoxycarbonylphenylboronic acid (493 mg, 2.69 mmol) for 3 h at 100° C. Flash chromatography of the residue on silica gel ($SiO_2$, hexane:ethyl acetate, 9:1) afforded 365 mg of ethyl 4-(thiazole-2-yl)benzoate as a white solid (70% yield). EM (IE): m/z (%): 233.1; (M+, 100).

Example 21

Preparation of ethyl 4-(5-(p-tolyl)thiazole-2-yl)benzoate (compound D with $R_1$=4-methylphenyl and $R_2$=4-ethoxycarbonyl, compound ($D_f$))

In a sealed tub was added ethyl 4-(thiazol-2-yl)benzoate (100 mg, 0.43 mmol), 4-methyliodobenzene (111 mg, 0.51 mmol), silver carbonate (236 mg, 0.86 mmol) and tetrakis (triphenylphosphine)palladium (0) (11.2 mg, 0.86 mmol). The flask was purged with nitrogen three times and then was added acetonitrile (1.8 mL). The mixture was stirred under Ar atmosphere for 12 h at 60° C. When the reaction completed, the inorganic solids were filtered on (Celite®) and the residue was washed several times with dichloromethane, then filtered and evaporated. Flash chromatography of the residue on silica gel ($SiO_2$, hexane:ethyl acetate, 9:1) afforded 115.8 mg of ethyl 4-(5-(p-tolyl)thiazol-2-yl)benzoate as a white crystalline solid (84% yield). EM (IE): m/z (%): 323.1; (M+, 100). HRMS (ESI): calculated for $C_{19}H_{18}NO_2S$: 324.1053. found: 324.1055.

Example 22

Preparation of ethyl 4-(4,4,5-trifluoro-5-(p-tolyl)-4,5-dihydrothiazol-2-yl)benzoate (compound (I) with $R_1$=4-methylphenyl and $R_2$=4-ethoxycarbonylphenyl, compound ($I_f$))

The compound of the title was prepared in a similar way to example 4 from d ethyl 4-(5-(p-tolyl)thiazol-2-yl)benzoate (50 mg, 0.15 mmol) and Selectfluor® (131.3 mg, 0.35 mmol) in ACN for 2.5 h at 80° C. Flash chromatography of the residue on silica gel ($SiO_2$, hexane:ethyl acetate, 95:5), afforded 10 mg of ethyl 4-(4,4,5-trifluoro-5-(p-tolyl)-4,5-dihydrothiazol-2-yl)benzoate as a white solid (17% yield). $^1$H-RMN (CDCl$_3$, 400 MHz): δ 8.19; (d, J=8.5 Hz, 2H), 8.06; (d, J=8.4 Hz, 2H), 7.60; (d, J=8.0 Hz, 2H), 7.29; (d, J=8.1 Hz, 2H), 4.43; (q, J=7.1 Hz, 2H), 2.42; (s, J=10.9 Hz, 3H), 1.43; (t, J=7.1 Hz, 3H). $^{19}$F-RMN (CDCl$_3$, 400 MHz): δ −80.45; (dd, J=219.2, 9.7 Hz), −104.41, (dd, J=219.1, 8.5 Hz), −130.39; (m). HRMS (ESI): calculated for $C_{19}H_{16}F_3NO_2S$: 380.0854. found: 380.0925.

Example 23

Preparation of tert-butyl 2-(4-(4,4,5,5-tetramethyl-1,3,2-dioxaborolan-2-yl)phenoxy)acetate To a solution of 4-(4,4,5,5-tetramethyl-1,3,2-dioxaborolan-2-yl)phenol (440 mg, 2.00 mmol) in anhydrous THF (40 mL) was added NaH (160 mg, 4.00 mmol). The reaction was stirred for 10 minutes at room temperature. Then, tert-butyl-bromoacetate was added and the mixture was stirred for 18 h at room temperature. Then, extracted with ethyl acetate (4×20 mL) and the organic layers were washed with an aqueous saturated solution of NaCl (3×20 mL), dried over $Na_2SO_4$, filtered and evaporated under reduced pressure. Flash chromatography of the residue on silica gel ($SiO_2$, hexane:ethyl acetate, 9:1) afforded 96.3 mg of tert-butyl 2-(4-(4,4,5,5-tetramethyl-1,3,2-dioxaborolan-2-yl)phenoxy)acetate as a white solid (74% yield). $RMN^1H$ ($CDCl_3$, 400 MHz): δ: 7.86-7.59; (m, 2H), 6.95-6.78; (m, 2H), 4.53; (s, 2H), 1.33; (s, 12H) ppm.

Example 24

Preparation of tert-butyl 2-(4-(thiazol-2-yl)phenoxy)acetate

To a solution of 2-bromothiazole (265 μL, 2.97 mmol), tert-butyl 2-(4-(4,4,5,5-tetramethyl-1,3,2-dioxaborolan-2-yl)phenoxy)acetate (1.19 g, 3.56 mmol), KCl (664.7 mg, 8.91 mmol) in a 4:1 mixture of toluene (20 mL)/EtOH (5 mL) was added an aqueous solution of $Na_2CO_3$ 2M (11.8 mL). The flask was evacuated and re-filled with nitrogen three times and then, tetrakis(triphenylphosphine)palladium (0) (346.2 mg, 0.30 mmol) was added. The reaction mixture was heated to 100° C. for 4 h. When the reaction was completed, inorganic solids were removed by filtration through Celite® and washing with several portions of dichloromethane, then the solvent was evaporated. The residue was absorbed onto silica then subjected to flash chromatography ($SiO_2$, hexane: ethyl acetate (AcOEt), 9:1) to afford 825.2 mg of de tert-butyl 2-(4-(thiazol-2-yl)phenoxy)acetate as a white solid (95% yield). $RMN^1H$ ($CDCl_3$, 400 MHz): δ 7.95-7.86; (m, 2H), 7.81; (d, J=3.3 Hz, 1H), 6.99-6.85; (m, 1H), 4.57; (s, 2H), 1.49; (s, 1H) ppm.

Example 25

Preparation of tert-butyl 2-(4-(5-(4-chlorophenyl)thiazol-2-yl)phenoxy)acetate To a solution of tert-butyl 2-(4-(thiazol-2-yl)phenoxy)acetate (360 mg, 1.23 mmol) and 1-chloro-4-iodobenzene (412.5 mg, 1.73 mmol) in anhydrous acetonitrile (ACN) (5.2 mL) was added $PPh_3$ (32.74 mg, 124 μmol) and $Ag_2CO_3$ (685.2 mg, 2.46 mmol). The flask was evacuated and re-filled with nitrogen three times and then $PdCl_2dppf$ was added (50.5 mg, 0.062 mmol). The reaction mixture was heated under Ar atmosphere for 72 h at 60° C. When the reaction was completed, the reaction mixture was filtered through Celite® (inorganic solids were removed) and the precipitate was washed with several portions of dichloromethane(3×20 mL). The filtrate was evaporated, and the residue was absorbed onto silica then subjected to flash chromatography ($SiO_2$, hexane: ethyl acetate (AcOEt), 9:1) to afford 322.5 mg of tert-butyl 2-(4-(5-(4-chlorophenyl)thiazol-2-yl)phenoxy)acetate as a yellow solid (76% yield). $RMN^1H$ ($CDCl_3$, 400 MHz): δ 7.94; (s, 1H), 7.92-7.87; (m, 2H), 7.56-7.46; (m, 2H), 7.42-7.35; (m, 2H), 7.01-6.93; (m, 2H), 4.57; (d, J=3.6 Hz, 2H), 1.50; (s, 9H) ppm.

Example 26

Preparation of tert-butyl 2-(4-(5-(4-chlorophenyl)-4,4,5-trifluoro-4,5-dihydrothiazol-2-yl)phenoxy)acetate, compound ($I_g$))

To a solution of tert-butyl 2-(4-(5-(4-chlorophenyl)thiazol-2-yl)phenoxy)acetate (78 mg, 190 μmol) in anhydrous ACN (5 mL) was added Selectfluor® (170.2 mg, 456 μmol). The reaction was stirred for 3 h at 60° C. When the reaction was completed, it was diluted with diethyl ether (50 mL) and washed with $H_2O$ (3×10 mL). The organic extracts were dried over $Na_2SO_4$, filtered and evaporated under reduced pressure The residue was absorbed onto silica then subjected to flash chromatography ($SiO_2$, hexane:AcOEt, 9:1), obtaining 8.6 mg of tert-butyl 2-(4-(5-(4-chlorophenyl)-4,4,5-trifluoro-4,5-dihydrothiazol-2-yl)phenoxy)acetate as a white solid (10% yield).

$RMN^1H$ ($CDCl_3$, 400 MHz): δ 7.95; (d, J=8.9 Hz, 2H), 7.64; (d, J=8.1 Hz, 2H), 7.44; (d, J=8.3 Hz, 2H), 7.00; (d, J=8.9 Hz, 2H), 4.62; (s, 2H), 1.50; (s, 9H) ppm. $RMN^{19}F$ ($CDCl_3$, 400 MHz): δ −78.53; (dd, J=217.0, 9.8 Hz), −103.16; (dd, J=217.4, 7.6 Hz), −131.00; (m, J=7.5 Hz) ppm.

Example 27

Preparation of 2-(4-(5-(4-chlorophenyl)-4,4,5-trifluoro-4,5-dihydrothiazol-2-yl)phenoxy)acetic acid To a solution of tert-butyl 2-(4-(5-(4-chlorophenyl)thiazol-2-yl)phenoxy)acetate (160 mg, 370 μmol) in anhydrous ACN (7 mL) was added Selectfluor® (327.8 mg, 880 μmol). The reaction was stirred for 15 h at 80° C. When the reaction was completed, it was diluted with diethyl ether and washed with $H_2O$ (3×10 mL). The organic extracts were dried over $Na_2SO_4$, filtered and evaporated under reduced pressure. The residue was absorbed onto silica then subjected to flash chromatography ($SiO_2$, hexane:AcOEt, 1:1), obtaining 52.2 mg of 2-(4-(5-(4-chlorophenyl)-4,4,5-trifluoro-4,5-dihydrothiazol-2-yl)phenoxy)acetic acid as a white solid (35% yield). $RMN^1H$ ($CDCl_3$, 400 MHz): δ 7.97 (d, J=8.1 Hz, 2H), 7.64; (d, J=8.1 Hz, 2H), 7.44; (d, J=8.3 Hz, 2H), 7.04; (d, J=7.9 Hz, 2H), 4.78; (s, 2H) ppm.

$RMN^{19}F$ ($CDCl_3$, 400 MHz): δ −78.73; (dd, J=217.2, 9.6 Hz), −103.25; (dd, J=217.1, 8.6 Hz), −131.00; (m, J=9.2 Hz) ppm.

Example 28

Preparation of N-butyl-2-(4-(5-(4-chlorophenyl)-4,4,5-trifluoro-4,5-dihydrothiazol-2-yl)phenoxy)acetamide, compound ($I_h$))

To a solution of 2-(4-(5-(4-chlorophenyl)-4,4,5-trifluoro-4,5-dihydrothiazol-2-yl)phenoxy)acetic acid (45.7 mg, 114 μmol) in DMF (5.7 mL) were added the coupling agents HOBt (18.4 mg, 136 μmol) and EDC.HCl (26.1 mg, 0.136 mmol). Then, butylamine was added (13.6 μL, 136 μmol) and the mixture was stirred for 2 h at room temperature. When the reaction was completed, it was diluted with dicloromethane (20 mL) and washed with $H_2O$ (3×5 mL). The organic extracts were dried over $Na_2SO_4$, filtered and evaporated under reduced pressure. The residue was absorbed onto silica then subjected to flash chromatography (SiO$_2$, hexane:A-cOEt, 6:4), obtaining 18.1 mg of N-butyl-2-(4-(5-(4-chlorophenyl)-4,4,5-trifluoro-4,5-dihydrothiazol-2-yl)phenoxy)acetamide (35% yield). RMN$^1$H (CDCl$_3$, 400 MHz): δ 8.03-7.93; (m, 2H), 7.64; (d, J=8.3 Hz, 2H), 7.45; (d, J=8.4 Hz, 2H), 7.09-7.01; (m, 2H), 6.48; (bs, 1H), 4.58; (s,), 3.53-3.26; (m, 2H), 1.59-1.50; (m, 2H), 1.41-1.34; (m, 2H), 0.98-0.90; (m, 3H) ppm. RMN$^{19}$F (CDCl$_3$, 400 MHz): δ −78.81; (dd, J=217.4, 9.8 Hz), −103.30; (dd, J=217.3, 8.8 Hz), −130.96; (m, J=9.3 Hz) ppm.

Example 29

Bioassays for the Detection of Antitumoral Activity

A screening of the antitumoral activity of compounds of formula (I) was carried out in Jurkat cells and a study of the most active compounds was performed in HeLa cells, TK6 cells, Ramos cells, MDA-MB 231 cells, T98-G cells, Hep3B cells and chronic lymphocytic leukemia (CLL) cells.
Cell Culture The human cell lines Jurkat (T lymphocytes from acute T cell leukemia), Ramos (B lymphocytes from Burkitt's lymphoma), TK6 (human lymphoblast cell line) HeLa (epithelial cervical carcinoma cell line), MDA-MB 231 (epithelial breast adenocarcinoma cell line), T98-G (glioblastoma cell line) and Hep3B (hepatocellular carcinoma cell line) were obtained from the European Collection of Cell Cultures.

Jurkat, Ramos, TK6 and CLL cells were grown in RPMI-1640 medium, and HeLa cells in DMEM medium, both containing 10% heat-inactivated fetal calf serum, 1% glutamine, and 1% penicillin-streptomycin. MDA-MB 231 cells were grown in DMEM/F-12 medium containing additionally 1% pyruvate. Hep3B cells were maintained in MEM medium supplemented with 10% fetal bovine serum. All were maintained at 37° C. in humidified atmosphere containing 5% carbon dioxide.
Patients with CLL and Cell Isolation Peripheral blood lymphocytes from CLL patients were obtained from the Haematology Unit at the IDIBELL-Hospital de Bellvitge, L'Hospitalet de Llobregat, Barcelona, Spain. CLL was diagnosed according to standard clinical and laboratory criteria. Written informed consent was obtained from all patients, in accordance with the Hospital de Bellvitge's Ethical Committee. Mononuclear cells from heparinized peripheral blood samples were isolated by centrifugation on a Ficoll-Hypaque (Seromed, Berlin, Germany) gradient. The purity of CLL samples was evaluated with allophycocyanin (APC)-conjugated anti-CD3 and phycoerythrin (PE)-conjugated anti-CD19 (Becton Dickinson, Frankiln Lakes, N.J., USA). Data were analysed by flow cytometry and the analysis was performed with the appropriate software.
Reagents Dimethyl sulfoxide (DMSO) was obtained from Sigma Chemicals Co. (St Louis, Mo., USA). Annexin V-FITC and propidium iodine (PI) were from Bender MedSystems (Vienna, Austria). Annexin V-APC was from eBioscience (St Diego, USA). Crystal violet was from Sigma-Aldrich.
Analysis of Apoptosis by Flow Cytometry 0.25-0.3×10$^6$ cells were washed in phosphate-buffered saline (PBS) and resuspended in 100 μl of annexin binding buffer and incubated with 1 μl of annexin V-Fluorescein-5-isothiocyanate (FITC) or annexin V-Allophycocyanin (APC). After 20 min of incubation in the dark at room temperature, 100 μl of annexin binding buffer with 5 μl of propidium iodide (PI) (20 μg/ml) was added just before flow cytometric analysis. Data were analyzed using the appropriate software. Cell viability was measured by analysis of phosphatidylserine exposure and PI uptake and it is expressed as the percentage of annexin-V and PI double-negative cells.

Apoptosis, or programmed cell death, is a general mechanism for removal of unwanted cells from the immune system. It is characterized by chromatin condensation, a reduction in cell volume, and endonuclease cleavage of DNA into oligonucleosomal length fragments. Apoptosis is also accompanied by a loss of membrane phospholipid asymmetry, resulting in the exposure of phosphatidylserine at the surface of the cell. Expression of phosphatidylserine at the cell surface plays an important role in the recognition and removal of apoptotic cells by macrophages. This is one of the earliest events of the apoptotic process. A method for the detection of apoptotic cells by flow cytometry uses the binding of fluorochrome-labeled annexin V to phosphatidylserine.

In addition, the plasmatic membrane is disrupted during late apoptosis but also during necrosis, so that it becomes permeable to substances such as PI. PI intercalates into double-stranded nucleic acids and is a fluorescent molecule with a molecular mass of 668.4 Da that can be used to stain DNA. It is excluded by viable cells but can penetrate cell membranes of dying or dead cells.

Thus, viable cells are annexin-V and PI double-negative cells, early apoptotic cells are annexin-V positive and PI negative cells whereas late apoptotic cells are annexin-V and PI double-positive cells. These three populations are indicative of apoptosis. A fourth population of PI positive cells correlates with necrotic cells.
Analysis of Cell Viability by Crystal Violet This method allows quantifying the amount of cells that survive after a toxic process, and it consists on cell staining with a colorant, crystal violet. This method is only useful when working with adherent cells that detached after undergoing a toxic process.

After the cells were incubated, in 12 or 24-well plates, with the different stimuli or inhibitors, the cell media was removed, and cells were washed twice with PBS. Then, a solution of Crystal violet at 0.2% (w/v) in 2% ethanol was added during 30 minutes. Following this, the staining solution was removed, and the wells were washed several times with PBS or distilled water until the excess staining that was not incorporated into the cells was eliminated. The plate was air-dried, and the stained cells were lysed in 10% SDS. By spectrophotometric analysis, the absorbance was measured at 595 nm.

The results were then calculated as the percentage of viable cells relative to control cells (cells incubated in the absence of treatment) at the indicated times.
Results
1. Screening Assay in Jurkat Cells by Measuring Cell Viability A screening of the effect of compounds $I_a$-$I_f$ was performed in Jurkat cell line (T lymphocytes form acute T cell leukemia) at a single dose of 40 μM for 24 hour-incubation. The structure of compounds $I_a$-$I_f$ are indicated in Table 1.

Two additional compounds were tested as comparative compounds: compound ($A_d$) which is a compound of formula (A) with $R_1$=$R_2$=chlorophenyl, and compound ($H_d$) which corresponds to the monofluorination of compound (A) where $R_1$=$R_2$=chlorophenyl.

Jurkat cells were selected among other leukemic tumor cell lines because they have the protein TP53 mutated.

Every compound mentioned above was dissolved in the minimum amount of DMSO necessary to be dissolved. Cell viability was measured by flow cytometry analysis. It was verified that the DMSO itself did not diminish the cell viability. Thus, all the observed effects on cell viability are due to the compounds' activity.

The results are summarized in Table 2: "+" means low activity; "++" means good activity and "+++" means very good activity; "−" means no activity.

TABLE 2

| Compound | Biological activity |
|---|---|
| $I_a$ | +++ |
| $I_b$ | +++ |
| $I_c$ | ++ |
| $I_d$ | +++ |
| $I_e$ | + |
| $I_f$ | ++ |
| comparative $H_d$ | − |
| comparative $A_d$ | − |

2. Dose-Response Analysis of compounds $I_a$, $I_b$, $I_c$, $I_d$, $I_e$ and $I_f$ The effect of the compounds $I_a$, $I_b$, $I_c$, $I_d$, $I_e$ and $I_f$ was deeply studied in different tumor cell lines.

Dose-response analysis was performed using Jurkat mutated-TP53 cancer cells and inactivated p53 cancer cell line HeLa.

Cell viability was measured by flow cytometry and it is expressed as the percentage of nonapoptotic cells (annexin-V negative) in respect to untreated cells at 24 hours. Therefore, values under 100% are indicative of apoptosis or loss of cell viability.

Jurkat cells (which are T lymphocytes from acute T cell leukemia with mutated TP53) were incubated with a range of doses from 1 to 40 µM of each compound for 24 hours. All of them induced apoptosis in a dose-dependent manner measured by flow cytometry (cf. FIG. 1).

HeLa cells (epithelial cervical carcinoma cell line with inactivated p53) were incubated with a range of doses from 2 to 40 µM of each compound for 24 hours. They induced apoptosis in a dose-dependent manner measured by flow cytometry (cf. FIG. 2).

The $IC_{50}$ at 24 hours was calculated for each compound using flow cytometry analysis. The results are expressed in Table 3 as the percentage of nonapoptotic cells (annexin-V negative) in respect to untreated cells at 24 hours.

TABLE 3

| | $IC_{50}$ (µM) | |
|---|---|---|
| Compound | Jurkat | HeLa |
| $I_a$ | 4 | 20 |
| $I_b$ | 3 | 8 |
| $I_c$ | 8 | 10 |
| $I_d$ | 3.5 | 1.75 |
| $I_e$ | 20 | 3.5 |
| $I_f$ | 8 | 17 |

Moreover, two representative compounds ($I_a$ and $I_d$) were tested in altered-TP53 cell lines Ramos, MDA-MB 231, T98-G and Hep3B, and in wild-type TP53 cancer cell line TK6. The study was completed using primary B-cells from CLL patients.

TK6 cells (human lymphoblast cell line with wild-type TP53) were incubated with a range of doses from 2 to 40 µM of compounds $I_a$ and $I_d$ for 24 hours. They induced apoptosis in a dose-dependent manner measured by flow cytometry (cf. FIG. 3).

Ramos cells (B lymphocytes from Burkitt's lymphoma with mutated TP53) were incubated with a range of doses from 2 to 40 µM of compounds $I_a$ and $I_d$ for 24 hours. They induced apoptosis in a dose-dependent manner measured by flow cytometry (cf. FIG. 4).

MDA-MB-231 cells (epithelial breast adenocarcinoma cell line with mutated TP53) were incubated with a range of doses from 2 to 60 µM of compounds $I_a$ and $I_d$ for 24 hours. They induced apoptosis in a dose-dependent manner measured by flow cytometry (cf. FIG. 5).

T98-G cells (glioblastoma cell line with mutated TP53) were incubated with a range of doses from 2 to 60 µM of compounds $I_a$ and $I_d$ for 24 hours. They induced apoptosis in a dose-dependent manner measured by flow cytometry (cf. FIG. 6).

Hep3B cells (hepatocellular carcinoma cell line with deleted TP53) were incubated with a range of doses from 2 to 40 µM of compounds $I_a$ and $I_d$ for 24 hours. They induced a loss on cell viability in a dose-dependent manner measured by crystal violet analysis (cf. FIG. 7).

B-CLL cells from patients with wild-type TP53 were incubated with a range of doses from 1 to 20 µM of compounds $I_a$ and $I_d$ for 24 hours. They induced apoptosis in a dose-dependent manner measured by flow cytometry (cf. FIG. 8).

CLL cells from patients with wild-type TP53 were incubated with a range of doses from 5 to 40 µM of compounds $I_c$ for 24 hours. It induced apoptosis in a dose-dependent manner measured by flow cytometry in B cells while T cells were less sensitive (cf. FIG. 9).

B-CLL cells from patients with mutated TP53 were incubated with a range of doses from 1 to 20 µM of compounds $I_a$ and $I_d$ for 24 hours. They induced apoptosis in a dose-dependent manner measured by flow cytometry (cf. FIG. 10).

The $IC_{50}$ of compounds $I_a$ and $I_d$ was calculated at 24 hours by flow cytometry analysis, except for Hep3B where crystal violet assay was used. The results are expressed in Table 4 as the percentage of viable cells in respect to untreated cells at 24 hours.

TABLE 4

| | $IC_{50}$ (µM) | | | | | |
|---|---|---|---|---|---|---|
| Compound | TK6 | Ramos | MDA-MB-231 | T98-G | Hep3B | B-CLL cells |
| $I_a$ | 8 | 4.5 | 16 | 50 | 14 | 4 |
| $I_d$ | 2.5 | 3.5 | 4 | 7.5 | 5 | 5 |

These results demonstrate that the family of thiazoline compounds of the present invention have antitumoral activity. Moreover, thiazoles-induced apoptosis is p53-independent, an important feature that makes a difference with most of the drugs currently used in cancer therapy, which mainly induce cell cycle arrest and apoptosis through p53 activation.

Example 30

Bioassays for the Detection of Antitumoral Activity of Compound $I_g$ and $I_h$

The effect of the compounds $I_g$ and $I_h$ was studied in two different tumor cell lines. Dose-response analysis was performed using Jurkat mutated-TP53 cancer cells and inactivated p53 cancer cell line HeLa.

Cell viability was measured by flow cytometry and it is expressed as the percentage of nonapoptotic cells (annexin-V

The invention claimed is:

1. A compound of formula (I) or a pharmaceutically acceptable salt thereof, or a stereoisomer thereof or a mixture of stereoisomers,

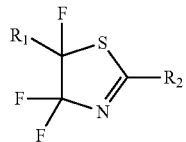

wherein:
R$_1$ is a radical selected from the group consisting of: phenyl, and phenyl mono-, di-, or tri-substituted by a radical independently selected from the group consisting of F, Cl, Br, I, (C$_1$-C$_6$)-alkyl, COO—(C$_1$-C$_6$)-alkyl, and (C$_1$-C$_6$)-alkoxy; and
R$_2$ is a radical selected from the same group as R$_1$, further including, a phenyl substituted in 4-position by a radical independently selected from the group consisting of —O(CH$_2$)CONH(CH$_2$)$_3$CH$_3$ and —OCH$_2$COOC(CH$_3$)$_3$, a biphenyl-4-yl, a thiazol-2-yl, and a thiazol-2-yl mono- or di-substituted, in 4 or 5 positions, by a radical selected from the group consisting of F and phenyl.

2. The compound of formula (I) as defined in claim 1, wherein: R$_2$ is a radical selected from the same group as R$_1$ further including a biphenyl-4-yl, a thiazol-2-yl, and a thiazol-2-yl mono- or di-substituted, in 4 or 5 positions, by a radical selected from the group consisting of F and phenyl.

3. The compound according to claim 2, wherein R$_1$ is selected from the group consisting of: phenyl, and phenyl mono-substituted by a radical independently selected from the group consisting of Cl, (C$_1$-C$_4$)-alkyl, and —COO—(C$_1$-C$_4$)-alkyl.

4. The compound according to claim 3, wherein R$_1$ is selected from the group consisting of: phenyl, 4-ethylphenyl, 4-chlorophenyl, 2-methylphenyl, 4-methylphenyl, 2-ethoxyphenylcarbonyl, and 4-ethoxyphenylcarbonyl.

5. The compound according to claim 2, wherein R$_2$ is a radical selected from the group consisting of: phenyl, and phenyl mono-substituted by a radical independently selected from the group consisting of Cl, (C$_1$-C$_4$)-alkyl, and COO—(C$_1$-C$_4$)-alkyl.

6. The compound according to claim 5, wherein R$_2$ is a radical selected from the group consisting of: phenyl, 4-ethylphenyl, 4-chlorophenyl, 2-methylphenyl, 4-methylphenyl, and 2-ethoxyphenylcarbonyl, and 4-ethoxyphenylcarbonyl.

7. The compound according to claim 2, wherein R$_2$ is biphenyl-4-yl.

8. The compound according to claim 2, wherein R$_2$ is 5-phenylthiazol-2-yl or 4-fluoro-5-phenylthiazol-2-yl.

9. The compound according to claim 1, wherein R$_2$ is phenyl substituted in 4 position by —O(CH$_2$)CONH(CH$_2$)$_3$CH$_3$ or by OCH$_2$COOC(CH$_3$)$_3$.

10. The compound according to claim 2, which is selected from the following table:

| Compound (I) | R$_1$ | R$_2$ |
|---|---|---|
| I$_a$ | Phenyl | 4-fluoro-5-phenylthiazol-2-yl |
| I$_b$ | Phenyl | 5-phenylthiazol-2-yl |
| I$_c$ | Phenyl | phenyl |
| I$_d$ | 4-chlorophenyl | 4-chlorophenyl |
| I$_e$ | Phenyl | biphenyl-4-yl |
| I$_f$ | 4-methylphenyl | 4-ethoxycarbonylphenyl. |

11. A method of treatment of a mammal for a cancer selected from the group consisting of leukemia, lymphoma, cervical carcinoma, breast adenocarcinoma, glioblastoma, and hepatocellular carcinoma, in a mammal suffering therefrom, the method comprising administering to the mammal a therapeutically effective amount of compound of formula (I), as defined in claim 1, together with pharmaceutically acceptable excipients or carriers.

12. A method of treatment according to claim 11, wherein the cancer is leukemia or lymphoma.

13. A method of treatment according to claim 11, wherein the leukemia or lymphoma are B-cell neoplasms.

14. A pharmaceutical composition comprising a therapeutically effective amount of the compound as defined in claim 1, together with adequate amounts of pharmaceutical excipients or carriers.

15. A preparation process of a compound of formula (I) as defined in claim 1, comprising:
a) first submitting a compound of formula (II), wherein X is an halogen,

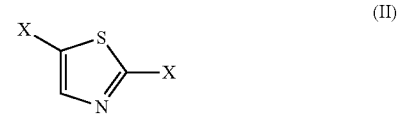

to a Suzuki coupling with a compound of formula R$_1$B(OH)$_2$, wherein R$_1$ has the same meaning as for compound (I), in the presence of a palladium catalyst, followed by submitting the compound obtained to a fluorination reaction with a fluorinating agent, to give a compound of formula (I) with R$_1$=R$_2$; or, alternatively,
b) first submitting a compound of formula (III)

to a Suzuki coupling with a compound of formula R$_2$B(OH)$_2$ wherein R$_2$ is a radical selected from the same group as R$_1$ further including biphenyl-4-yl, and R$_1$ having the same meaning as for compound (I), in the presence of a palladium catalyst, then halogenating the compound obtained with a halogen source, subsequently coupling the compound obtained with a compound of formula $R_1B(OH)_2$ wherein $R_1$ has the same meaning as for compound (I), in the presence of a palladium catalyst, and finally submitting the compound obtained to a fluorination reaction with a fluorinating agent to give a compound of formula (I) with $R_1$ different from $R_2$; or alternatively, c) first submitting a compound of formula (III) to a Suzuki coupling with a compound of formula $R_2B(OH)_2$ wherein $R_2$ is a radical selected from the same group as $R_1$ further including biphenyl-4-yl, and $R_1$ having the same meaning as for compound (I), in the presence of a palladium catalyst, then submitting the compound obtained to a C—H activation reaction with a compound of formula $R_1I$ wherein $R_1$ has the same meaning as for compound (I); and then submitting the compound obtained to a fluorination reaction with a fluorinating agent to give a compound of formula (I) with $R_1$ different from $R_2$; or alternatively, d) submitting a compound of formula (III) to a homocoupling reaction in the presence of a palladium catalyst, then halogenating the compound obtained with a halogen source, followed by submitting the compound obtained to a Suzuki coupling with a compound of formula $R_1B(OH)_2$, wherein $R_1$ has the same meaning as for compound (I), in the presence of a palladium catalyst, and, finally, by submitting the compound obtained to a fluorination reaction with a fluorinating agent to give a compound of formula (I) where $R_1$ is phenyl and $R_2$ a thiazol-2-yl substituted by a phenyl; and e) optionally, converting the compounds obtained in any of the processes a) to d) into a pharmaceutically acceptable salt by reaction of the compound (I) with a pharmaceutically acceptable acid or a pharmaceutically acceptable base to yield the corresponding pharmaceutically acceptable salt.

* * * * *